US008884027B2

(12) United States Patent
Crooks et al.

(10) Patent No.: US 8,884,027 B2
(45) Date of Patent: Nov. 11, 2014

(54) MELAMPOMAGNOLIDE B DERIVATIVES AS ANTILEUKEMIC AND CYTOTOXIC AGENTS

(75) Inventors: Peter A. Crooks, Nicholasville, KY (US); Craig T. Jordan, Webster, NY (US); Shanshan Pei, Rochester, NY (US); Shama Nasim, Lexington, KY (US)

(73) Assignees: University of Rochester, Rochester, NY (US); University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 13/279,038

(22) Filed: Oct. 21, 2011

(65) Prior Publication Data

US 2012/0122943 A1    May 17, 2012

Related U.S. Application Data

(60) Provisional application No. 61/405,978, filed on Oct. 22, 2010.

(51) Int. Cl.
*C07D 493/04* (2006.01)
*C07D 495/04* (2006.01)
*C07D 519/00* (2006.01)

(52) U.S. Cl.
CPC ............ *C07D 493/04* (2013.01); *C07D 519/00* (2013.01)
USPC ........ 548/304.1; 549/299; 548/526; 544/153; 514/232.8; 514/321; 514/338; 514/387; 514/468

(58) Field of Classification Search
USPC ........................................ 548/304.1; 549/299
See application file for complete search history.

(56) References Cited

U.S. PATENT DOCUMENTS

| | | | |
|---|---|---|---|
| 4,136,177 | A | 1/1979 | Lin |
| 4,255,415 | A | 3/1981 | Chrai |
| 4,668,506 | A | 5/1987 | Bawa |
| 4,713,224 | A | 12/1987 | Tamhankar |
| 4,788,603 | A | 11/1988 | Fujimura |
| 4,816,570 | A | 3/1989 | Farquhar |
| 4,931,279 | A | 6/1990 | Bawa |
| 4,968,788 | A | 11/1990 | Farquhar |
| 5,411,947 | A | 5/1995 | Hostetler |
| 5,463,092 | A | 10/1995 | Hostetler |
| 5,916,596 | A | 6/1999 | Desai |
| 6,096,331 | A | 8/2000 | Soon-Shiong |
| 6,312,662 | B1 | 11/2001 | Erion |
| 6,716,825 | B2 | 4/2004 | Hostetler |
| 6,752,981 | B1 | 6/2004 | Erion |
| 7,193,081 | B2 | 3/2007 | Kopcho |
| 7,214,668 | B2 | 5/2007 | Reddy |
| 7,312,242 | B2 | 12/2007 | Crooks |
| 7,678,904 | B2 | 3/2010 | Crooks |
| 7,758,891 | B2 | 7/2010 | Desai |

FOREIGN PATENT DOCUMENTS

| | | |
|---|---|---|
| WO | WO 90/00555 | 1/1990 |
| WO | WO 95/03036 | 2/1995 |
| WO | WO 96/39831 | 12/1996 |
| WO | WO 01/18013 | 3/2001 |
| WO | WO 03/090690 | 11/2003 |
| WO | WO 03/095665 | 11/2003 |

OTHER PUBLICATIONS

El-Feraly, CA 102:21216, 1985.*
Kwok et al., Chemistry & Biology, 2001, 8(8), pp. 759-766.*

* cited by examiner

*Primary Examiner* — Laura L. Stockton
(74) *Attorney, Agent, or Firm* — Meunier Carlin & Curfman, LLC

(57) ABSTRACT

Melampomagnolide B is disclosed as a new antileukemic sesquiterpene. A biotin-conjugated derivative of melampomagnolide B was prepared to elucidate its mechanism of action. Prodrugs of Melampomagnolide B are disclosed.

23 Claims, 11 Drawing Sheets

MELAMPOMAGNOLIDE B DERIVATIVES AS ANTILEUKEMIC AND CYTOTOXIC AGENTS

CROSS-REFERENCE TO RELATED APPLICATIONS

This application claims the benefit of U.S. provisional application Ser. No. 61/405,978 filed on Oct. 22, 2010, the entire contents of which are incorporated herein by reference.

STATEMENT REGARDING FEDERALLY SPONSORED RESEARCH OR DEVELOPMENT

This invention was made with government support under grant number W81XWH-07-1-0601, awarded by the United States Department of Defense; and under grant number C024964, awarded by the New York State Stem Cell Foundation. The government has certain rights in the invention.

BACKGROUND OF THE INVENTION

1. Field of the Invention

Melampomagnolide B (3) is disclosed as a new antileukemic sesquiterpene. A biotin-conjugated derivative (4) of melampomagnolide B was prepared to elucidate its mechanism of action. A study of the biochemical interactions of the biotin probe suggests that melampomagnolide B derives its remarkable selectivity for leukemic cells over normal hematopoietic cells from its unique ability to exploit biochemical differences between the two cell types. Prodrugs of Melampomagnolide B are disclosed.

2. Description of the Related Art

The past several years have seen a surge of interest in the anticancer properties of sesquiterpene lactones. A germacrenolide, parthenolide (PTL, 1) has been noted for its remarkable antileukemic properties. Skalska et al. *PLoS ONE,* 2009, 4, e8115. Initial efforts pertaining to the biomechanistic study of parthenolide and its analogs revealed that they seem to promote apoptosis by inhibiting the activity of the NF-kB transcription factor complex, and thereby down-regulating anti-apoptotic genes under NF-kB control. Bork et al. *FEBS Lett.* 1997, 402, 85; Wen, *J. Biol. Chem.,* 2002, 277, 38954; Hehner et al., *J. Biol. Chem.* 1998, 273, 1288; Sweeney et al., *Clin. Cancer Res.,* 2004, 10, 5501; Yip-Schneider et al., *Mol. Cancer. Ther.,* 2005, 4, 587; Nozaki et al., *Oncogene,* 2001, 20, 2178. Nuclear factor kB (NF-kB) is a transcriptional regulator that plays a central part in responses to inflammatory signaling.

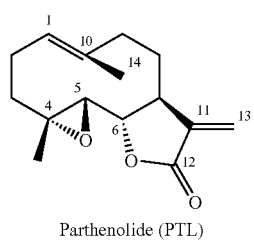

Parthenolide (PTL)

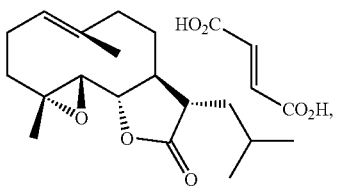

Dimethylaminoparthenolide (DMAPT) fumarate; LC-1

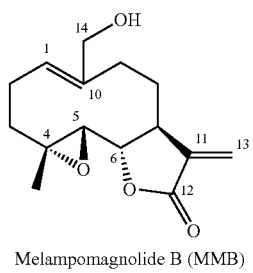

Melampomagnolide B (MMB)

Parthenolide induces robust apoptosis of primary acute myeloid leukemic (AML) cells. Guzman et al., *Blood,* 2005, 105, 4163; Guzman and Jordan, *Exp. Opin. Biol. Ther.,* 2005, 5, 1147. In particular, parthenolide causes cell death in AML stem and progenitor cells in vitro, with minimal toxicity towards normal hematopoietic cells. The apoptosis induced by parthenolide is not solely due to NF-kappaB inhibition, but rather arises from a broad set of biological responses, which likely include activation of p53 and an increase in reactive oxygen species. Parthenolide has also been the source of several novel antileukemic compounds arising from our program over the past decade. For example, parthenolide analogs were prepared by adding amines to the exocyclic olefin of the enone function of 1, thereby rendering the resulting compounds water-soluble. Neelakantan et al., *Bioorg. Med. Chem. Lett.,* 2009, 19, 4346; Nasim and Crooks, *Bioorg. Med. Chem. Lett.,* 2008, 18, 3870. Such adducts showed retention of antileukemic properties of parthenolide; in particular, the dimethylamine-adduct of parthenolide (DMAPT, LC-1, 2), which has progressed to phase-I clinical trials in the United Kingdom for the treatment of AML, ALL and CLL. Neelakantan et al., 2009.

Unfortunately, DMAPT has a relatively short in vivo half-life (approximately two hours) which may limit its activity. Moreover, the design of this molecule does not readily afford opportunities to develop tissue-targeting strategies due to stability problems associated with drug formulation. This is related to the ability of the drug to undergo reverse Michael deamination reactions to generate parthenolide. Thus, there is a need to both improve the biological activity of PTL and create novel pharmacological agents with drug-like characteristics that can be formulated as oral dosage forms.

One PTL analog that was synthesized via selenium oxide oxidation was a C10 hydroxymethyl derivative. Notably, hydroxylation of the C10 methyl group of PTL resulted in the concomitant conversion of the geometry of the C9-C10 double bond from trans to cis. The resulting product, a hydroxymethyl 1(10)-cis-parthenolide analog, has previously been reported as melampomagnolide B (MMB). Melampomagnolide B (MMB, 3) is a melampolide originally isolated from *Magnolia grandiflora*. El-Feraly, *Phytochemistry,* 1984, 23, (10); 2372-2374.

It is herein disclosed that melampomagnolide B (MMB, 3) has been identified as a new antileukemic sesquiterpene with properties similar to parthenolide (PTL, 1). Further, as a functionalized analog of PTL, the MMB molecule allows the synthesis of conjugated analogs that retain biological activity.

SUMMARY OF THE INVENTION

Melampomagnolide B is disclosed as a new antileukemic sesquiterpene. A biotin-conjugated derivative of melampomagnolide B was prepared to elucidate its mechanism of action. Prodrugs of Melampomagnolide B are disclosed.

The disclosure provides a compound of the formula (I):

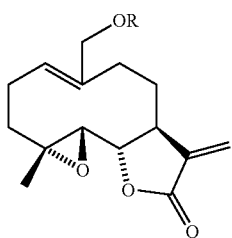
(I)

wherein: R is selected from —P(O)(OR$^1$)(OR$^2$); —CH$_2$OP(O)(OR$^1$)(OR$^2$); —C(O)(CR$^3$R$^4$)$_n$X; —CH$_2$OC(O)(CR$^3$R$^4$)$_n$ X; —C(O)O(CR$^3$R$^4$)$_n$X or —C(O)(CH$_2$)$_m$C(O)NH(CR$^3$,R$^4$)$_n$X; R$^1$, R$^2$ are independently selected from H; a pharmaceutically acceptable cation; or optionally substituted C$_1$-C$_{12}$alkyl, alkenyl, alkynyl, heterocycloalkyl, heteroaryl, cycloalkyl, aryl; R$^3$, R$^4$ are independently selected from H, NR$^5$R$^6$, OR$^1$, SR$^1$, S(O)R$^1$, SO$_2$R$^1$, or optionally substituted C$_1$-C$_{12}$alkyl, alkenyl, alkynyl, heterocycloalkyl, heteroaryl, cycloalkyl, aryl; R$^5$, R$^6$ are independently selected from H; or optionally substituted C$_1$-C$_{12}$alkyl, alkenyl, alkynyl, heterocycloalkyl, heteroaryl, cycloalkyl, aryl; —CO$_2$C$_1$-C$_{12}$alkyl, CO$_2$alkenyl, CO$_2$alkynyl, CO$_2$heterocycloalkyl, CO$_2$heteroaryl, CO$_2$cycloalkyl, CO$_2$aryl; C$_1$-C$_{12}$alkylamino or R$^5$ and R$^6$ optionally together with the nitrogen atom form an optionally substituted 5-12 membered ring, said ring optionally comprising 1 or more heteroatoms; X is selected from H, NR$^5$R$^6$, NC(O)R$^1$; NC(O)OR$^1$; OR$^1$, SR$^1$, halo, trifluoromethyl, or optionally substituted C$_1$-C$_{12}$alkyl, alkenyl, alkynyl, heterocycloalkyl, heteroaryl, cycloalkyl, aryl; n is 0-12; m is 1-2; or a pharmaceutically acceptable salt, ester or prodrug thereof.

In one aspect, R is selected from —P(O)(OR$^1$)(OR$^2$) or —CH$_2$OP(O)(OR$^1$)(OR$^2$). In another aspect, R$^1$, R$^2$ are independently selected from H, Na, or optionally substituted C$_1$-C$_6$ alkyl. In certain specific aspects, R is

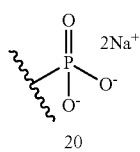
20

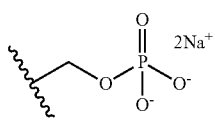
21

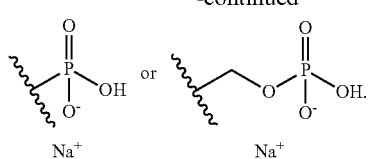

In one aspect, R is —C(O)(CR$^3$R$^4$)$_n$X. In another aspect, X is NR$^5$R$^6$, OR$^1$, or SR$^1$.

In specific aspects, R is selected from

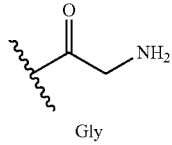
Gly
1

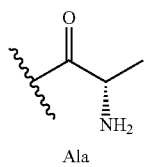
Ala
2

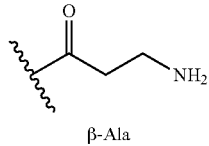
β-Ala
3

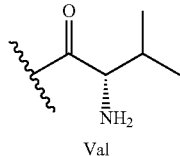
Val
4

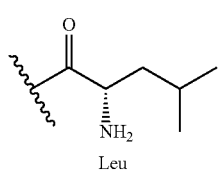
Leu
5

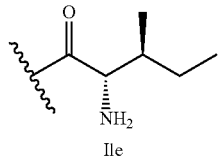
Ile
6

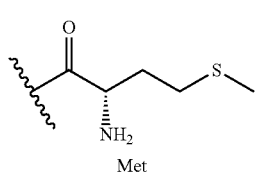
Met
7

-continued

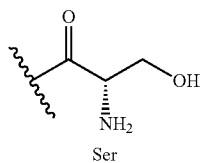
Ser

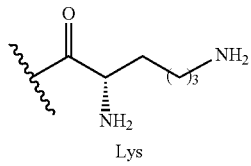
Lys

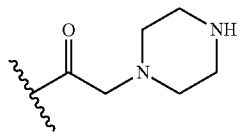

or

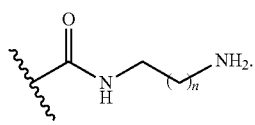

14 n = 1
15 n = 2
16 n = 3
17 n = 4

In another aspect, R is —CH$_2$OC(O)(CR$^3$R$^4$)$_n$X, and X is NR$^5$R$^6$. In a specific aspect R is

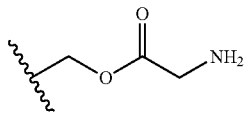

11

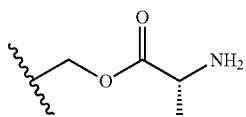

12

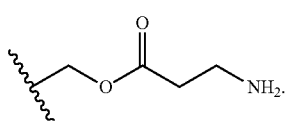

13

In another aspect, R is —C(O)O(CR$^3$R$^4$)$_n$X, wherein X is NR$^5$R$^6$. In a specific aspect, R is

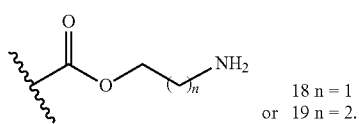

18 n = 1
or 19 n = 2.

In another aspect, R is or —C(O)(CH$_2$)$_m$C(O)NH(CR$^3$R$^4$)$_n$X, wherein X is NR$^5$R$^6$.

In a specific aspect, R is selected from

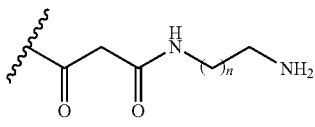

22 n = 1
23 n = 2

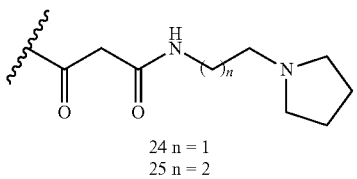

24 n = 1
25 n = 2

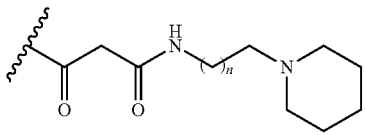

26 n = 1
27 n = 2

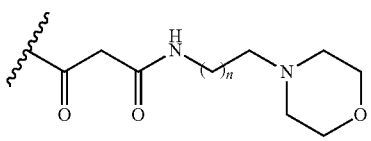

28 n = 1
29 n = 2

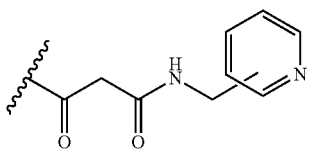

30 2-pyr
31 3-pyr
or 32 4-pyr.

In one aspect, R$^5$ and R$^6$ together with N form an optionally substituted ring. In one specific aspect, the ring is a monocyclic, bicyclic or tricyclic alkyl or aryl ring system, said ring system optionally substituted and optionally comprising one or more heteroatoms or a group selected from —CO—, —SO—, —SO$_2$—, and —PO—. In another specific aspect, R$_1$ and R$_2$ are —(CH$_2$)$_a$—Y—(CH$_2$)$_b$—; where Y is a heteroatom or a group selected from —CO—, —SO—, —SO$_2$— and —PO—; a is an integer 0 to 5; b is an integer 0 to 5; the sum of a and b being 0 to 5; and together with N form an optionally substituted ring, said ring optionally fused to a cycloalkyl or aryl group to form a bicyclic or tricyclic ring system, said system optionally substituted and optionally comprising one or more heteroatoms.

In another aspect, wherein X is NR$^5$R$^6$ the compound a pharmaceutically acceptable salt selected from hydrochloride, maleate, fumarate, or mesylate.

In another aspect, the disclosure provides a compound selected from

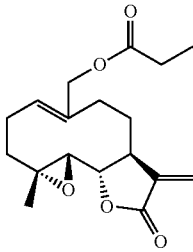

4

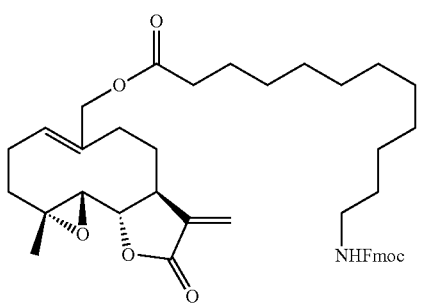

6

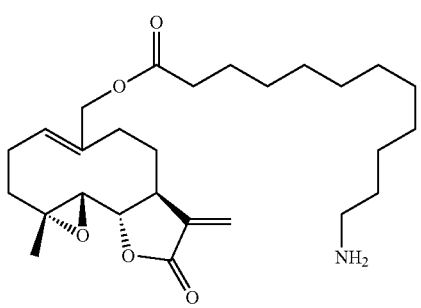

7 or

In one embodiment, the disclosure provides a pharmaceutical composition comprising a compound of formula (I) or a pharmaceutically acceptable salt thereof; in combination with a pharmaceutically effective diluent or carrier.

In another embodiment, the disclosure provides a method of inhibiting cancer cell growth, comprising administering to a mammal afflicted with cancer, an amount of a compound of formula (I) effective to inhibit the growth of said cancer cells. In one aspect, the disclosure provides a method of inhibiting cancer cell growth comprising contacting said cancer cell in vitro or in vivo with an amount of a compound of formula (I) effective to inhibit the growth of said cancer cell.

In another aspect, the disclosure provides a method of treating an aberrant inflammatory condition, comprising administering to a mammal in need thereof, an amount of a compound of formula (I) effective to reduce, prevent or control said condition. In one aspect, the aberrant inflammatory condition is an autoimmune disorder, said method comprising administering to a mammal an amount of a compound of formula (I) effective to reduce, prevent or control said autoimmune disorder.

In certain aspects, the disclosure provides a compound of formula (I):

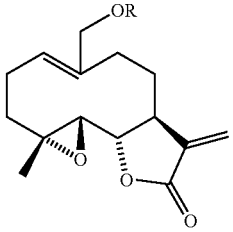

(I)

wherein R is a group that is cleaved to a hydroxy group under physiological conditions during or after administration to a mammalian patient, thereby yielding Melampomagnolide B; wherein R is selected from —P(O)(OR$^1$)(OR$^2$); —CH$_2$OP(O)(OR$^1$)(OR$^2$); —C(O)(CR$^3$R$^4$)$_n$X; —CH$_2$OC(O)(CR$^3$R$^4$)$_n$ X; —C(O)O(CR$^3$R$^4$)$_n$X or —C(O)(CH$_2$)$_m$C(O)NH(CR$^3$R$^4$)$_n$X; R$^1$, R$^2$ are independently selected from H; a pharmaceutically acceptable cation; or optionally substituted C$_1$-C$_{12}$alkyl, alkenyl, alkynyl, heterocycloalkyl, heteroaryl, cycloalkyl, aryl; R$^3$, R$^4$ are independently selected from H, NR$^5$R$^6$, OR$^1$, SR$^1$, S(O)R$^1$, SO$_2$R$^1$, or optionally substituted C$_1$-C$_{12}$alkyl, alkenyl, alkynyl, heterocycloalkyl, heteroaryl, cycloalkyl, aryl; R$^5$, R$^6$ are independently selected from H; or optionally substituted C$_1$-C$_{12}$alkyl, alkenyl, alkynyl, heterocycloalkyl, heteroaryl, cycloalkyl, aryl; —CO$_2$C$_1$-C$_{12}$alkyl, CO$_2$alkenyl, CO$_2$alkynyl, CO$_2$heterocycloalkyl, CO$_2$heteroaryl, CO$_2$cycloalkyl, CO$_2$aryl; C$_1$-C$_{12}$alkylamino or R$^5$ and R$^6$ optionally together with the nitrogen atom form an optionally substituted 5-12 membered ring, said ring optionally comprising 1 or more heteroatoms; X is selected from H, NR$^5$R$^6$, OR % SR % halo, trifluoromethyl, or optionally substituted C$_1$-C$_{12}$alkyl, alkenyl, alkynyl, heterocycloalkyl, heteroaryl, cycloalkyl, aryl; n is 0-6; m is 1-2; or a pharmaceutically acceptable salt, ester or prodrug thereof.

In another embodiment, the disclosure provides a method of drug delivery comprising administering to a mammal, an amount of a compound of formula (I):

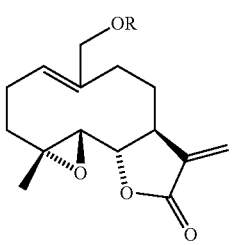

(I)

wherein R is a group that is cleaved to a hydroxy group under physiological conditions during or after administration to a mammalian patient, thereby yielding Melampomagnolide B; wherein the substituents are as described above.

In another embodiment, the disclosure provides a method of treating bone marrow in human bone marrow transplant treatment of leukemia, the method comprising treating bone marrow with a compound of claim 1 prior to reintroduction of bone marrow to patient. In another embodiment, the disclosure provides a method of treating a patient having chronic or acute myeloid leukemia (CML/AML) or acute lymphoblastic leukemia (ALL), comprising administering to the patient, an effective amount of a compound of formula (I).

In a further embodiment, the disclosure provides a method of treating a patient having chronic or acute myeloid leukemia (CML/AML) or acute lymphoblastic leukemia (ALL), comprising administering to the patient, an effective amount of melampomagnolide B.

In another embodiment, the disclosure provides a method of inhibiting angiogenesis in a patient in need thereof, comprising administering to the patient, an effective amount of a compound of formula (I).

In another embodiment the disclosure provides a method of inhibiting angiogenesis in a patient in need thereof, comprising administering to the patient, an effective amount of a compound of melampomagnolide B

BRIEF DESCRIPTION OF THE DRAWINGS

FIG. 3A shows immunoblot of phosphorylated p65 subunit of the NF-kB complex and actin. FIGS. 3B-D shows viability of primary leukemia cells after overnight culture at varying concentrations.

DETAILED DESCRIPTION OF THE DISCLOSURE

Definitions

Figure 1:
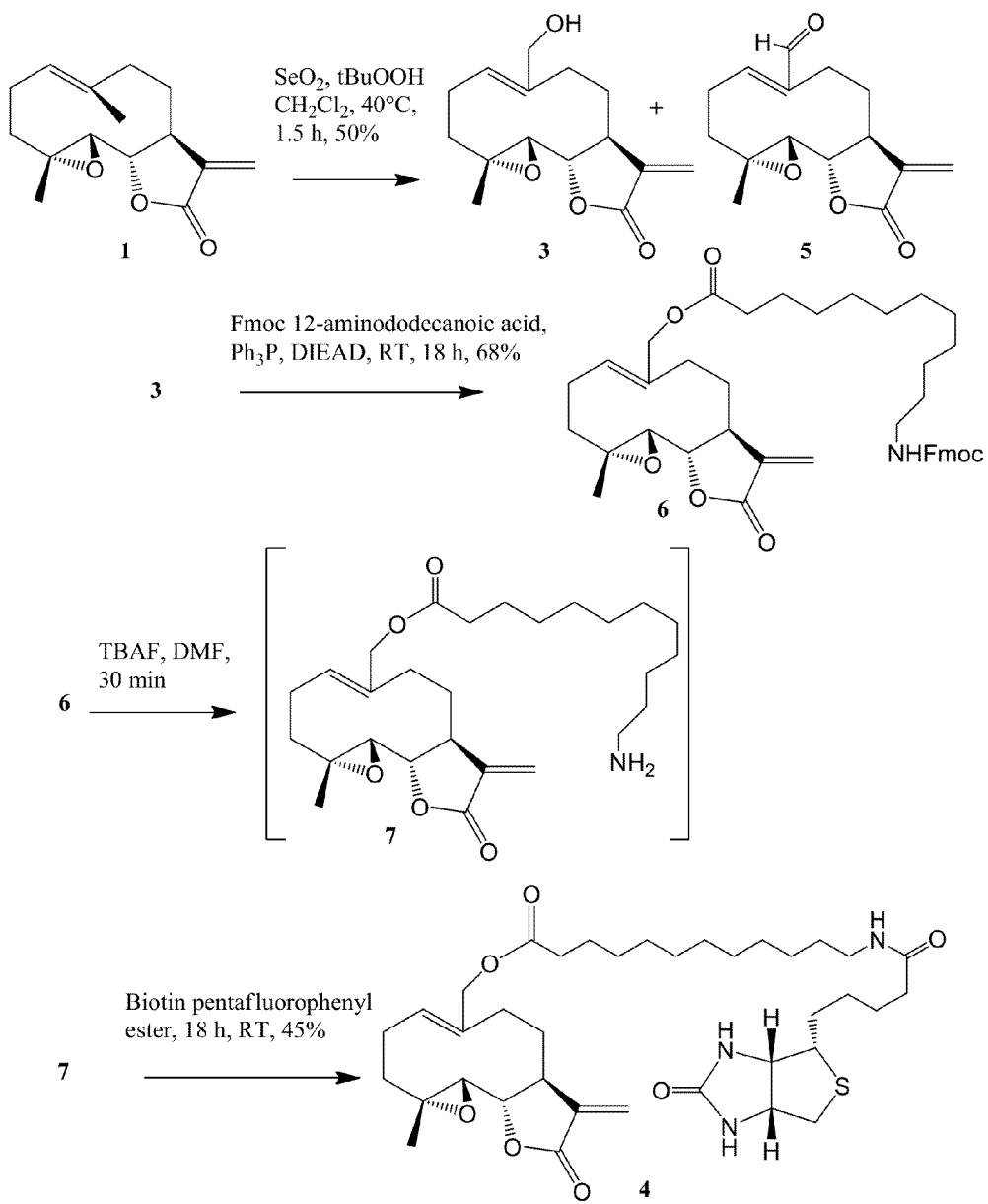
FIG. 1 shows a route of synthesis of melampomagnolide B (MMB, 3) from parthenolide (PTL, 1), and conjugation of biotin to 3.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "aliphatic" or "aliphatic group" as used herein means a straight-chain or branched $C_{1-12}$ hydrocarbon chain that is completely saturated (alkyl) or that contains one or more units of unsaturation (alkenyl, alkynyl), or a monocyclic $C_{3-8}$ hydrocarbon or bicyclic $C_{8-12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl," "alkoxy," "hydroxyalkyl," "alkoxyalkyl" and "alkoxycarbonyl," used alone or as part of a larger moiety include both straight and branched chains containing one to eighteen carbons; one to twelve carbon atoms; one to six carbons or one to four carbons. The terms "alkenyl" and "alkynyl" used alone or as part of a larger moiety shall include both straight and branched chains containing two to twelve carbon atoms.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I.

The term "heteroatom" means nitrogen, oxygen, or sulfur and includes any oxidized form of nitrogen and sulfur, and the quaternized form of any basic nitrogen. Heteroatom further includes Se, Si and P.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl.

The term "heterocycloalkyl," "heterocycle," "heterocyclyl" or "heterocyclic" as used herein means monocyclic, bicyclic or tricyclic ring systems having five to fourteen ring members in which one or more ring members is a heteroatom, or C=O, wherein each ring in the system contains 3 to 7 ring members and is non-aromatic. Examples of heterocycloalkyl include pyrrolidinyl, imidazolidinyl, tetrahydrofuranyl, triazolidinyl, 1,3-dioxolanyl, piperidinyl, piperazinyl, morpholinyl, dioxanyl, hexahydropyrimidinyl; each optionally substituted with H, $C_1$-$C_6$ alkyl, cycloalkyl, hydroxy, amino, halo or trifluoromethyl groups.

The term "heteroaryl," used alone or in combination with other terms, refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic". Examples of heteroaryl rings include 2-furanyl, 3-furanyl, 2-imidazolyl, 4-imidazolyl, 5-imidazolyl, 3-isoxazolyl, 4-isoxazolyl, isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. The term "heteroaralkyl" refers to an alkyl group substituted by a heteroaryl. The term "heteroarylalkoxy" refers to an alkoxy group substituted by a heteroaryl.

An aryl (including aralkyl, aralkoxy, aryloxyalkyl and the like), heteroaryl (including heteroaralkyl, heteroarylalkoxy and the like), or heterocycloalkyl (including heterocycle, heterocyclyl or heterocyclic and the like) group may contain one or more substituents. Suitable substituents on an unsaturated carbon atom of an aryl, heteroaryl, aralkyl or heteroaralkyl-group are selected from halogen; haloalkyl; H; —$CF_3$; —R; —OR; —SR; 1,2-methylenedioxy; 1,2-ethylenedioxy; protected OH (such as acyloxy); phenyl (Ph); Ph substituted with R; —O(Ph); —O—(Ph) substituted with R; —$CH_2$(Ph); —$CH_2$(Ph) substituted with R; —$CH_2CH_2$(Ph); —$CH_2CH_2$(Ph) substituted with R; —$NO_2$; —CN; —N(R)$_2$; —NRC(O)R; —NRC(O)N(R)$_2$; —$NRCO_2$R; —NRNRC(O)R; —NR—NRC(O)N(R)$_2$; —$NRNRCO_2$R; —C(O)C(O)R; —C(O)$CH_2$C(O)R; —$CO_2$R; —C(O)R; —C(O)N(R)$_2$; —OC(O)N(R)$_2$; —S(O)$_2$R; —$SO_2$N(R)$_2$; —S(O)R; —$NRSO_2$N(R)$_2$; —$NRSO_2$R; —C(=S)N(R)$_2$; —C(=NH)—N(R)$_2$; —(CH$_2$)$_y$NHC(O)R; —(CH$_2$)$_y$R; —(CH$_2$)$_y$NHC(O)NHR; —(CH$_2$)$_y$NHC(O)OR; —(CH$_2$)$_y$NHS(O)R; —(CH$_2$)$_y$NHSO$_2$R; or —(CH$_2$)$_y$NHC(O)CH((V)$_z$—R)(R) wherein each R is independently selected from hydrogen, optionally substituted $C_{1-6}$ aliphatic, an unsubstituted 5-6 membered heteroaryl or heterocyclic ring, phenyl (Ph), —O(Ph), or —$CH_2$(Ph)—$CH_2$(Ph), wherein y is 0-6; z is 0-1; and V is a linker group. When R is $C_{1-6}$ aliphatic, it may be substituted with one or more substituents selected from —$NH_2$, —NH($C_{1-4}$ aliphatic), —N($C_{1-4}$ aliphatic)$_2$, —S(O)($C_{1-4}$ aliphatic), —$SO_2$($C_{1-4}$ aliphatic), halogen, ($C_{1-4}$ aliphatic), —OH, —O($C_{1-4}$ aliphatic), —$NO_2$, —CN, —$CO_2$H, —$CO_2$($C_{1-4}$ aliphatic), —O(halo $C_{1-4}$ aliphatic), or -halo($C_{1-4}$ aliphatic); wherein each $C_{1-4}$ aliphatic is optionally.

An aliphatic group, including alkyl, alkenyl, alkynyl or a non-aromatic heterocyclic ring may contain one or more substituents. Suitable substituents on a saturated carbon of an aliphatic group or of a non-aromatic heterocyclic ring are selected from those listed above for the unsaturated carbon of an aryl or heteroaryl group and the following: =O, =S, =NNHR, =NN(R)$_2$, =N—, =NNHC(O)R, =NNHCO$_2$(alkyl), =NNHSO$_2$(alkyl), or =NR, where each R is independently selected from hydrogen or an optionally substituted $C_{1-6}$ aliphatic. When R is $C_{1-6}$ aliphatic, it may be substituted with one or more substituents selected from —$NH_2$, —NH($C_{1-4}$ aliphatic), —N($C_{1-4}$ aliphatic)$_2$, halogen, —OH, —O—($C_{1-4}$ aliphatic), —$NO_2$, —CN, —$CO_2$H, —$CO_2$($C_{1-4}$ aliphatic), —O(halo $C_{1-4}$ aliphatic), or -halo($C_{1-4}$ aliphatic); wherein each $C_{1-4}$ aliphatic is optionally substituted.

Substituents on a nitrogen of a non-aromatic heterocyclic ring are selected from —R, —N(R)$_2$, —C(O)R, —C(O)OR, —C(O)C(O)R, —C(O)CH$_2$C(O)R, —SO$_2$R, —SO$_2$N(R)$_2$, —C(=S)N(R)$_2$, —C(=NH)—N(R)$_2$ or —NRSO$_2$R; wherein each R is independently selected from hydrogen, an optionally substituted $C_{1-6}$ aliphatic, optionally substituted phenyl (Ph), optionally substituted —O(Ph), optionally substituted —CH$_2$(Ph), optionally substituted —CH$_2$CH$_2$(Ph), or an unsubstituted 5-6 membered heteroaryl or heterocyclic ring. When R is a $C_{1-6}$ aliphatic group or a phenyl ring, it may be substituted with one or more substituents selected from —$NH_2$, —NH($C_{1-4}$ aliphatic), —N($C_{1-4}$ aliphatic)$_2$, halogen, —($C_{1-4}$ aliphatic), —OH, —O—($C_{1-4}$ aliphatic), —$NO_2$, —CN, —$CO_2$H, —$CO_2$($C_{1-4}$ aliphatic), —O(halo $C_{1-4}$ aliphatic) or -halo($C_{1-4}$ aliphatic); wherein each $C_{1-4}$ aliphatic is optionally substituted.

The term "linker group" or "linker" means an organic moiety that connects two parts of a compound. Linkers include alkylidene chain that is a saturated or unsaturated, straight or branched, $C_{1-8}$ carbon chain which is optionally substituted, and wherein up to two non-adjacent saturated carbons of the chain are optionally replaced by R* wherein R* is —C(O)—, —C(O)C(O)—, —C(O)NR—, —C(O)NRNR—, —C(O)O—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—; wherein R is selected from hydrogen or optionally substituted aliphatic, cycloalkyl, heterocycloalkyl, aryl or heteroaryl, and preferably H or optionally substituted $C_{1-4}$ aliphatic. Optional substituents on the alkylidene chain are as described above for an aliphatic group. Alternatively, the linker group is R*.

The term "treatment" refers to any treatment of a pathologic condition in a mammal, particularly a human, and includes: (i) preventing the pathologic condition from occurring in a subject which may be predisposed to the condition but has not yet been diagnosed with the condition and, accordingly, the treatment constitutes prophylactic treatment for the disease condition; (ii) inhibiting the pathologic condition, i.e., arresting its development; (iii) relieving the pathologic condition, i.e., causing regression of the pathologic condition; or (iv) relieving the conditions mediated by the pathologic condition.

The term "therapeutically effective amount" refers to that amount of a compound of the invention that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable salts" includes, but is not limited to, salts well known to those skilled in the art, for example, mono-salts (e.g. alkali metal and ammonium salts) and poly salts (e.g. di- or tri-salts) of the compounds of the invention. Pharmaceutically acceptable salts of compounds of formulas (I), (II), (III), or (IV) are where, for example, an exchangeable group, such as hydrogen in —OH, —NH—, or —P(=O)(OH)—, is replaced with a pharmaceutically acceptable cation (e.g. a sodium, potassium, or ammonium ion) and can be conveniently be prepared from a corresponding compound of formula (I) by, for example, reaction with a suitable base. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, mesylate, acetate, citrate, malate, malonate, fumarate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts include quaternary ammonium salts formed with R'Y; where Y is selected from halogen, tosylate, methanesulfonate, benzenesulfonate, trifluoromethanesulfonate and the like; and R' is selected from an optionally substituted cycloalkyl, heterocycloalkyl, aryl or heteroaryl.

Suitable acids include hydrofluoric acid, hydrochloric acid, hydrobromic acid, hydriodic acid, sulfuric acid, nitric acid, phosphoric acid, carbonic acid, boric acid, selenious acid, hydrogen sulfide, phosphomolybdic acid, phosphorous acid, sulfurous acid, citric acid, maleic acid, D-malic acid, L-lactic acid, D-lactic acid, DL-lactic acid, oxalic acid, methanesulfonic acid, valeric acid, oleic acid, lauric acid, para-toluenesulfonic acid, 1-naphthalensulfonic acid, 2-naphthalensulfonic acid, phthalic acid, tartaric acid, L-malic acid, DL-malic acid, malonic acid, succinic acid, fumaric acid, glycolic acid, thioglycolic acid, glycine, sarcocine, sulfonic acid, nicotinic acid, picolinic acid, isonicotinic acid, benzoic acid and substituted benzoic acid where benzene ring bears one or more substituents.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The term "prodrug" or "prodrugs" is used in its ordinary meaning in the art and means a compound of the invention that has at least one functional moiety masked or protected by another moiety that is designed to be cleaved under particular physiological conditions, leaving the deprotected or unmasked compound of the invention. The use of masking agents is common and well-known in the art, for example, masking charged groups such as phosphate or phosphonate groups. All such masking agents are suitable and can be used with the compounds of the invention. Various agents such as acyloxy alkyl esters are described by Srivasta et al., (1984 *Bioorganic Chemistry* 12, 118-12), and by Freeman et al. (1997 *Progress in Medicinal Chemistry* 34:112-147) which are each incorporated in their entirety herein by reference; and 3-phthalidyl phosphonate esters are described by Dang Q., et al., (1999 *Bioorganic & Med. Chem. Letters*, 9:1505-1510), which is incorporated in its entirety herein by reference. For example, and not by way of limitation, Srivasta et al. also describe acetoxymethyl, isobutryloxymethyl, and pivaloxymethyl as masking agents. Other suitable masking groups comprising pivaloxyalkyl, e.g., pivaloxymethyl, or a pivaloyloxy group as described by Farquhar D. et al., (1995 *J. Med. Chem.*, 38:488-495) which is incorporated in its entirety herein by reference. Still other masking or protecting agents are described in U.S. Pat. Nos. 4,816,570 and 4,968,788 both of which are incorporated in their entirety herein by reference. Lipid prodrugs are also suitable for use with the compounds of the invention. By non-limiting example, certain lipid prodrugs are described in Hostetler et al., (1997 *Biochem. Pharm.* 53:1815-1822), and Hostetler et al., 1996 *Antiviral Research* 31:59-67), both of which are incorporated in their entirety herein by reference. Additional examples of suitable prodrug technology is described in WO 90/00555; WO 96/39831; WO 03/095665A2; U.S. Pat. Nos. 5,411,947; 5,463,092; 6,312,662; 6,716,825; and U.S. Published Patent Application Nos. 2003/0229225 and 2003/0225277 each of which is incorporated in their entirety herein by reference. Such prodrugs may also possess the ability to target the drug compound to a particular tissue within the patient, e.g., liver, as described by Erion et al., (2004 *J. Am. Chem. Soc.* 126: 5154-5163; Erion et al., *Am. Soc. Pharm. & Exper. Ther. DOI:* 10.1124/jept.104.75903 (2004); WO 01/18013 A1; U.S. Pat. No. 6,752,981), each of which is incorporated in their entirety herein by reference. By way of non-limiting example, other prodrugs suitable for use with the compounds of the invention are described in WO 03/090690; and by Harris et al., (2002 *Antiviral Chem & Chemo.* 12: 293-300; Knaggs et al., 2000 *Bioorganic & Med. Chem. Letters* 10: 2075-2078) each of which is incorporated in their entirety herein by reference.

The term "drug-likeness" refers to the concept that drugs share specific molecular properties that distinguish them from other natural or synthetic chemicals. A drug-like molecule has properties such as optimal solubility to both water and fat, for example an orally administered drug must be absorbed through the intestinal lining, be carried in aqueous blood and penetrate the lipid cellular membrane of the cell. To be sufficiently soluble in aqueous media such as blood and intracellular fluid, solubility in water can be estimated from the number of e.g. hydrogen bond donors compared to alkyl side-chains in the molecule. However, too many H-bond donors can lead to low fat solubility, so the drug may not be able to penetrate the cell wall efficiently. In addition, the drug-like molecule must be of a smaller molecular weight. A traditional method to evaluate drug-likeness is to check compliance with Lipinski's Rule of Five, which covers the number of hydrophilic groups, molecular weight and hydrophobicity.

Detailed Description

Acute myelogenous leukemia (AML) is a life-threatening disorder in which normal blood-formation (hematopoiesis) is subverted by malignant transformation of normal stem or Progenitor cells. Although an enormous amount of research has been conducted in the area of therapeutic agents for AML, the standard of care has not substantially changed in over 30 years. Regimens based on a combination of cytarabine (ara-C) and an anthracycline are still considered the best frontline option for most patients, despite the relatively poor long-term prognosis (5 year survival of approximately 20%) (Lowenberg et al., 1999). Thus, new options for treatment of AML are a high priority. Notably, clinical development of experimental therapeutics is very fast in AML, due to the poor prognosis and rapid disease progression for late stage patients. Therefore, initial testing in AML not only affords the opportunity to evaluate leukemia stem cell (LSC) targeting, but also has the practical advantage of promoting rapid clinical advancement for promising new agents.

Previously, the naturally-occurring (plant derived) compound parthenolide (PTL) was investigated with respect to anti-leukemia properties. PTL was found to be highly effective for induction of cell death of primary human AML specimens (Guzman et al., 2005). Importantly, at comparable doses, PTL shows little to no toxicity to normal hematopoietic cells, suggesting that non-specific side effects should be relatively low. Furthermore, PTL was shown to be equally effective amongst all subpopulations found within primary AML specimens, including the so-called leukemia stem cell (LSC). Studies over the past decade have strongly implicated a relatively rare LSC population as the key driving force in both the genesis of AML, as well as relapse following conventional therapy (Dick, 2005). Indeed, several laboratory-based studies have demonstrated that LSC are resistant to both cytarabine and anthracyclines, and that drug regimens which more effectively eradicate LSC lead to improved outcome (Costello et al., 2000; Ishikawa et al., 2007). Therefore, agents that can effectively target the LSC population are of particular interest for the treatment of AML patients.

Although one focus has been on development of treatment for AML, PTL has demonstrated activity for virtually every form of cancer. Indeed, the basic properties of PTL in cancer were first reported in 1973 (Wiedhopf et al., 1973), and now appear in over 100 publications. These studies have demonstrated pre-clinical activity of PTL for cancers of the breast, lung, prostate, colon, blood, liver, kidney, pancreas, brain, and bone (Patel et al., 2000; Sweeney et al., 2004, 2005; Yoshikawa et al., 2007; Oka et al., 2007; Parada-Turska et al., 2007; Suvannasankha et al., 2008; Wang et al., 2009; Zhang et al., 2009). Thus, PTL not only eradicates LSC, but also bulk AML cells and many other types of cancer.

Detailed SAR studies of PTL were performed to better understand the basic chemistry required to mediate anti-leukemia activity. Studies indicated that the α-methylene-γ-lactone moiety is critical for the function of PTL, as this structure is known to mediate Michael addition reactions (Neelakantan et al., 2009). In biological systems, the consequences of this reactivity are most prevalent for free thiols and cysteine residues. In addition, it was demonstrated that the epoxide ring is also quite important for PTL activity, since loss of the epoxide ring resulted in at least a 10-fold reduction in anti-leukemia activity; molecular modeling data suggests that the epoxide moiety may be a critical structural element in providing the active molecular conformation of PTL. Unfortunately, PTL is relatively water-insoluble and has poor bioavailability and drug-likeness. A series of PTL analogs was previously prepared with the goal of creating a more therapeutically useful derivative (Neelakantan et al., 2009). The most promising candidate to arise from these studies was dimethylaminoparthenolide (DMAPT, LC-1, 2), which demonstrated nearly 1000-fold greater water solubility than PTL when formulated as a fumarate salt. In addition, DMAPT retains virtually identical anti-leukemia properties as PTL, including the ability to selectively target LSCs. Pharmacological studies in rats and dogs demonstrated that DMAPT is 70% orally bioavailable, and well tolerated at doses resulting in serum concentrations of up to 10-fold excess of the biologically active concentration (Guzman et al., 2007b). Based on these findings, DMAPT has advanced to phase 1 clinical trials, and is currently being evaluated in patients with advanced hematologic malignancies. DMAPT and certain PTL analogs are disclosed in U.S. Pat. Nos. 7,312,242 and 7,678,904, each of which is incorporated herein by reference.

Despite the characterization of DMAPT, there is still significant opportunity for further development of parthenolide-based compounds. DMAPT has a relatively short in vivo half-life (approximately two hours) which may limit its activity. Moreover, the design of this molecule does not readily afford opportunities to develop tissue-targeting strategies due to stability problems associated with drug formulation. This is related to the ability of the drug to undergo reverse Michael deamination reactions to generate parthenolide.

MMB (3) was identified during the course of SAR studies based on parthenolide (PTL, 1). In performing such studies, one PTL analog that was synthesized via selenium oxide oxidation was a $C_{10}$ hydroxymethyl derivative. Notably, hydroxylation of the C10 methyl group of PTL resulted in the concomitant conversion of the geometry of the $C_9$-$C_{10}$ double bond from trans to cis. The resulting product, a hydroxymethyl 1(10)-cis-parthenolide analog, has previously been reported as melampomagnolide B (MMB, 3). El-Feraly, 1984.

Figure 2:
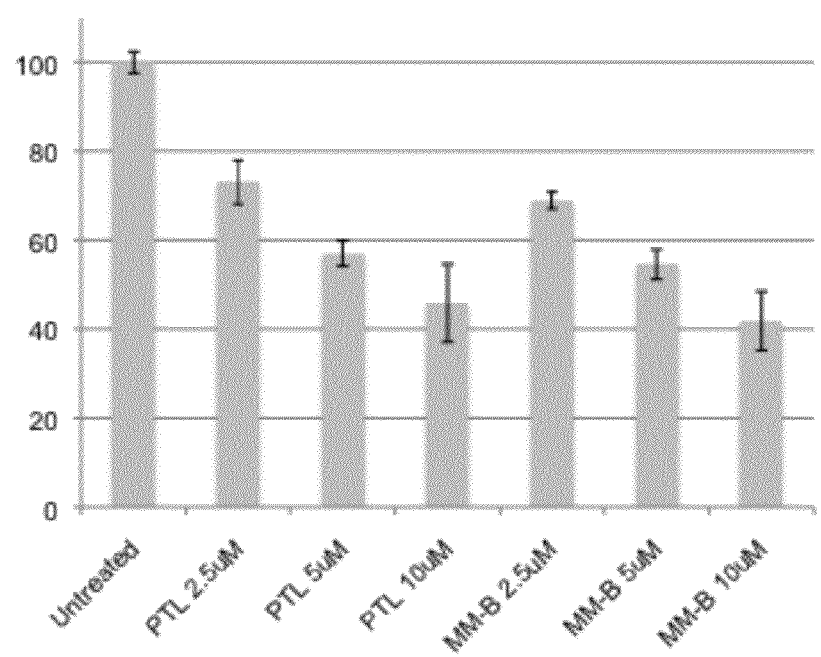
FIG. 2 shows viability of primary AML specimens when treated for 18 hours with either PTL, 1, or MMB, 3, compared to control, untreated cells.

MMB has been found to exhibit identical anti-leukemia activity compared to PTL, as shown in FIG. 2. In one embodiment, the disclosure provides pharmaceutical compositions and methods of treating leukemia and other cancers with MMB. Unfortunately, like PTL, MMB does not possess good drug-like properties for oral administration, as determined by the Lipinsky's "rule of five". Lipinski et al., Experimental and computational approaches to estimate solubility and permeability in drug discovery and development settings. *Adv. Drug. Deliv. Rev.* 23:3-25, 1997.

MMB exhibits a C14-OH substituent, which provides opportunities for synthetic derivatization strategies. In one aspect, the disclosure provides MMB derivatives for the treatment leukemia and cancer. In one aspect, water soluble MMB prodrugs are disclosed. In another aspect, the disclosure provides MMB derivatives for the characterization of leukemia and cancer cells. In this aspect, the disclosure provides tissue-targeting MMB derivatives. In one specific aspect, a biotinylated MMB analog is prepared and utilized as a laboratory tool to identify MMB target proteins in AML cells. This approach has been extremely useful in providing a better understanding of the underlying mechanisms by which the anti-leukemia (and anti-LSC) activity of PTL and its derivatives is achieved.

MMB was synthesized from commercially available PTL by $SeO_2$/tBuOOH oxidation based on previous literature reports as shown in FIG. 1. Gonzales et al., *Tetrahedron*, 44:4585-4589, 1988; Kwok et al., The anti-inflammatory natural product parthenolide from the medicinal herb Feverfew directly binds to and inhibits IκB kinase. *Chem Biol*, 8:759-766, 2001. There is a discrepancy in the literature regarding the geometry of the 1(10)-double bond in MMB. Gonzales et al., 1988 and Neukirch et al., 2003 reported complete double bond isomerization during the oxidation of PTL, i.e., from 1(10)-trans in PTL to 1(10)-cis in MMB. Neukirch et al., Transannular cyclization in cyclodecenes: The case study of melampolides. *Eur J Org Chem*, 3969-3975, 2003. However, the study from Kwok et al. indicated that the configuration of the double bond was retained on conversion of PTL to MMB under the above conditions. Since the NMR spectra of MMB obtained in our hands were identical to those reported by Kwok et al. we performed X-ray crystal analysis on MMB and confirmed the occurrence of double bond isomerization, as shown in the structure of MMB (3) below.

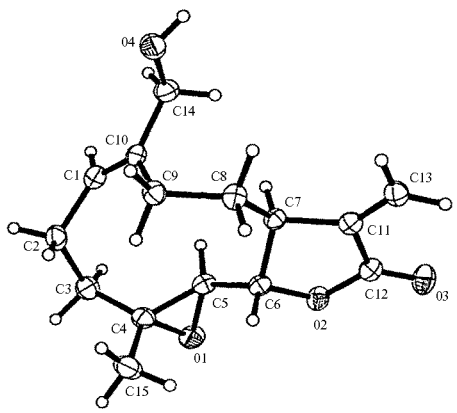

Configuration of MMB, 3, Confirmed by X-Ray Crystal Analysis.

Similar to PTL, MMB is also sparingly soluble in aqueous media, which limits its usefulness for oral delivery, the preferred route of drug administration. Based on in silico calculations, there is a predicted 35% chance that the oral bioavailability of MMB will be >30%, with a mere 6% chance that oral bioavailability will be >70% (predicted by Pharma algorithms' ADME-Tox calculator). The predicted poor oral bioavailability likely results from low aqueous solubility, since this causes a low dissolution-rate, which is often the rate-limit step during oral drug absorption. Fleisher et al., Improved oral drug delivery: solubility limitations overcome by the use of prodrugs. *Adv Drug Deliv Rev*, 19:115-130, 1996; Taylor, Improved passive oral drug delivery via prodrugs. *Adv Drug Deliv Rev*, 19:131-148, 1996. Furthermore, low water solubility can itself be a source of toxicity, due to precipitation of the drug, causing crystalluria. Müller C E. Prodrug approaches for enhancing the bioavailability of drugs with low solubility. *Chem Biodiversity*, 6:2071-2083, 2009.

Higher water solubility results in a higher driving force (concentration gradient) in the intestinal lumen for absorption compared to low water solubility. Fleisher et al., 1996. Moreover, many lipophilic drugs are substrates for the multi-drug resistant 1 (MDR1) gene product P-glycoprotein (P-gp), which can limit systemic drug exposure after oral dosing. Lown et al., Role of intestinal P-glycoprotein (Mdr1) in inter-patient variation in the oral bioavailability of cyclosporine. *Clin Pharmacol Ther*, 62:248-260, 1997; Ekins et al., Three-dimensional quantitative structure-activity relationships of inhibitors of P-glycoprotein. *Mol Pharmacol*, 61:964-973, 2002.

In one embodiment, the disclosure provides a strategy for overcoming the low aqueous solubility, and as a result, improving oral bioavailability of MMB. In one aspect, the water-insoluble parent drug MMB is converted into soluble prodrugs by attaching a water-solubilizing pro-moiety to the C14-OH group of MMB. It should be also noted that the free C14-OH group on MMB could possibly lead to poor oral bioavailability because it may be a substrate for phase 2 glucuronidation and sulfation metabolic pathways during the oral absorption process. Thus, in a related aspect, a water-solubilizing pro-moiety conjugated at the C14-OH group of MMB may also protect the parent drug from rapid first pass metabolism during absorption, leading to improved bioavailability.

In one embodiment, the disclosure provides prodrugs of MMB in which the prodrug moiety has been conjugated to the allylic hydroxyl function, and which have been designed to improve the oral bioavailability and drug-likeness of MMB. A prodrug is defined as pharmacologically inactive molecule that is converted into an active drug entity via metabolic biotransformation. In one aspect, the water soluble MMB derivative is inactive. In another aspect, the water soluble MMB derivative exhibits activity. In yet another aspect, the water-soluble MMB derivatives of the disclosure are cleaved under physiological conditions to revert to MMB. The utility of prodrugs and their specific design, usually address a particular problem or flaw in the drug-like characteristics of the parent active compound. Such problems may include poor aqueous solubility, poor absorption and distribution, rapid first-pass metabolism, instability, and formulation problems. For prodrugs that are to be utilized as oral dosage forms, the prodrug-to-drug conversion should occur after absorption from the gastrointestinal (GI) tract. Thus, the prodrug should be designed to possess optimal drug absorption characteristics through the GI mucosa into plasma, and should exhibit maximal stability while in the GI tract. Once in the plasma, the prodrug should undergo facile enzymatic cleavage to liberate the active drug molecule. Such characteristics can be achieved by appropriate design of the prodrug moiety.

The anti-leukemia activity of MMB itself is excellent, and indistinguishable from PTL. In one embodiment, the disclosure provides for the use of MMB as an antileukemic agent. In one aspect, the disclosure provides MMB conjugated analogs that retain biological, anti-leukemic and anti-cancer activity. In one aspect, derivatives and prodrugs of MMB can be prepared via conjugation at the allylic hydroxyl group.

In one embodiment, MMB derivatives of the disclosure are useful for the treatment of AML and/or in other forms of leukemia. In one aspect, MMB and/or derivatives thereof are useful for the treatment of other forms of cancer, for example, cancers of the breast, lung, prostate, colon, blood, liver, kidney, pancreas, brain, and bone.

Prodrugs of MMB

Figure 8:
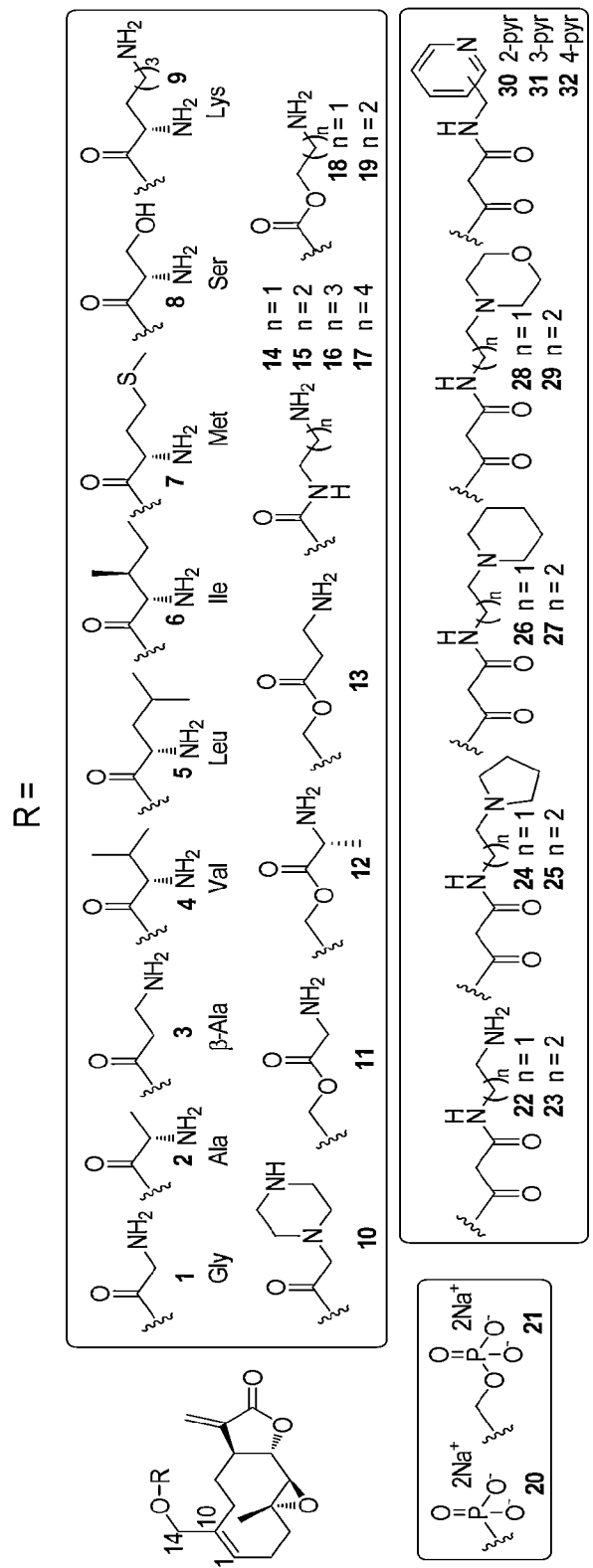
FIG. 8 shows derivatives of MMB. Various ester, ether, carbamate, carbonate and phosphate MMB derivatives are proposed to act as water-soluble, orally bioavailable MMB prodrugs.

In one aspect, the disclosure provides derivatives and prodrugs of MMB. Certain prodrugs and/or derivatives of MMB are shown in FIG. 8. Rational for these MMB prodrugs includes, for example, a computational screen utilizing Pharma Algorithms' ADME-Tox calculator that was conducted in order to identify virtual 'hits' (i.e. prodrugs with acceptable "predicted" oral bioavailability). Amino acid (AA) esters of MMB (1-10), AA esters incorporating a methylene dioxide (a formaldehyde equivalent) spacer (11-13), amino carbamate MMB prodrugs (14-17), and amino carbonate MMB prodrugs (18 and 19) all had good oral bioavailability based on the ADME-Tox computational predictions (Table 2). As described previously, from PTL to the ionizable dimethylamine derivative DMAPT (Guzman et al., 2007b; Neelakantan et al., 2009), water solubility increases nearly 1000-fold. Thus, these ionizable amine-containing prodrugs are all expected to have dramatically increased water-solubility compared to MMB. In addition, AA ester prodrugs have the potential to further increase oral bioavailability due to active absorption by transporters (e.g., small peptide transporter PEPT1). For example, the valine-containing prodrugs valacyclovir and valganciclovir are substrates for the enzyme PEPT1 (Reusser, 2001; Terada and Inui, 2004; Tsume et al., 2008). These AA containing prodrugs are expected to be hydrolyzed to the parent drug by aminopeptidase enzymes in the brush border membrane of the GI tract. Prodrugs which can penetrate into the peripheral circulation by passive permeation and/or by active transport will then be rapidly hydrolyzed by various peptidase enzymes in plasma. Table 1 shows the predicted percentage probability of possessing oral bioavailability (% F) greater than 30% and 70% for MMB and representative water-soluble MMB prodrugs (ADME-Tox calculator).

TABLE 1

Predicted percentage probability of possessing oral bioavailability (% F)

| Compounds | %; Probability of % F > 30% | %; Probability of % F > 70% |
|---|---|---|
| MMB | 35% | 3% |
| Prodrug 1 | 72% | 63% |
| Prodrug 10 | 35% | 21% |
| Prodrug 11 | 61% | 42% |
| Prodrug 15 | 61% | 18% |
| Prodrug 19 | 61% | 11% |
| Prodrug 20 | 3% | 1% |
| Prodrug 22 | 37% | 4% |

Two types of phosphate prodrugs of MMB (20 and 21) are shown in FIG. 8. According to ADME-Tox computational data, the oral bioavailability of these two prodrugs is poor (Table 1), which is not surprising, given the fact that the prediction by ADME-Tox calculator is mainly based on the physicochemical proprieties of the molecule. Since phosphoric acid is a highly polar and extensively ionized pro-moiety, phosphate prodrugs should have significantly decreased membrane permeability compared to the parent drug. However, phosphate esters have been shown to be very effective at improving the delivery of poorly water-soluble parent drug molecules after oral delivery. Numerous examples can be found in the literature (Stella and Nti-Addae, 2009). The reasons for the success of phosphate esters as oral prodrugs are: 1) oral absorption will not be limited by dissolution-rate, since phosphate prodrugs are highly soluble in GI tract fluids; 2) phosphate esters are chemically stable enough to prevent the precipitation of the parent drug in the GI tract; 3) most importantly, phosphates are rapidly hydrolyzed by membrane-bound alkaline phosphatases, which are in abundance on the brush border surface of the cells lining the small intestine, i.e. the enterocytes. Thus, the more permeable parent drug will be released, and will readily cross the enterocyte membranes and enter the systemic circulation.

The disclosure also provides prodrugs which contain a self-cleavable spacer and a water solubilizing moiety, to maintain the prodrug in a soluble form in the GI tract fluids. These types of MMB prodrugs will gradually revert to the lipophilic parent drug without precipitation (22-32, FIG. 8). The increased solubility of the prodrug and the high membrane permeability of the well-dispersed and lipophilic parent drug will provide a higher driving force for it to be readily absorbed via the intestinal lumen (Sohma et al., 2003). Conversion of prodrug-to-parent drug involves a chemical cleavage at the self-cleavable spacer through a unique intramolecular cyclization-elimination reaction via imide formation under physiological conditions (Sohma et al., 2003) (FIG. 9A). The conversion time is tunable by modifying the structure of the solubilizing moiety, the bond length of the spacer, the pKa of the amine group, and the pH of the medium. Although the in silico predicted bioavailability is low (Table I), it is likely to be much higher when one takes into account the unique pH-dependent and tunable hydrolysis mechanism. Also, the generation of parent drug does not rely on enzyme action, which may be an advantage in dealing with genetic variability associated with enzymatic prodrug hydroysis in plasma.

Figure 9:
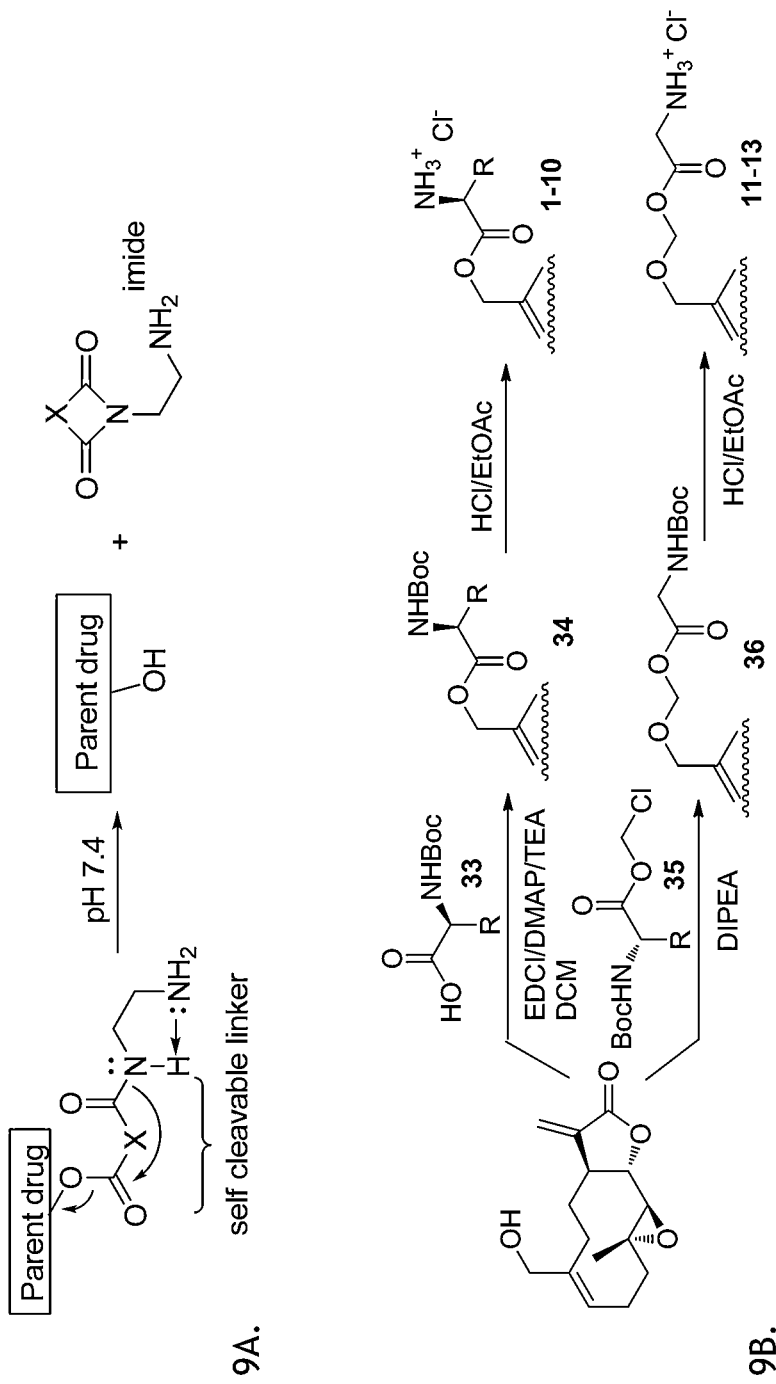
FIG. 9A shows conversion of prodrug-to-parent drug involves a chemical cleavage at the self-cleavable spacer through a intramolecular cyclization-elimination reaction via imide formation under physiological conditions.
FIG. 9B shows synthesis of prodrugs 1-13 from FIG. 8. Prodrugs 1-10 can be synthesized by Steglich esterification of MMB with an appropriate amino group protected AA to afford compound 34, followed by deprotection of the amino group. Reaction of MMB with an appropriate Boc-AA chloromethyl ester 35 will afford compound 36, which upon deprotection will furnish prodrugs 11-13.
Figure 10:
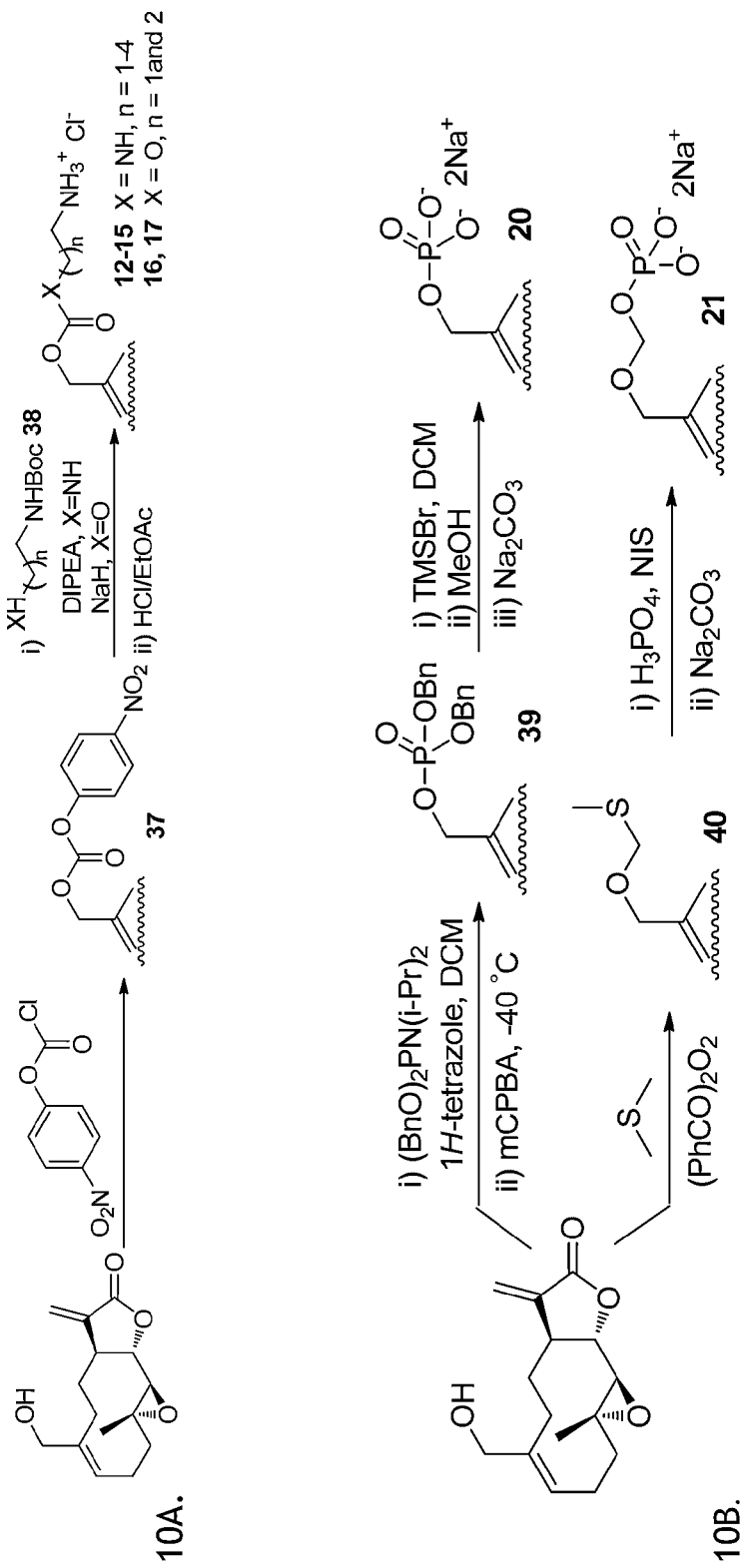
FIG. 10A shows synthesis of prodrugs 14-19 from FIG. 8. Carbamate prodrugs 14-17 and carbonate prodrugs 18 and 19 can be prepared from the substitution reaction between mono-Boc protected diamine or N-Boc aminopropanol (38) and 4-nitrophenyl MMB carbonate (37), followed by deprotection. Compound 37 can be prepared by reacting MMB with 4-phenyl chloroformate.
FIG. 10B shows synthesis of prodrugs 20 and 21 from FIG. 8. Phosphate prodrug 20 can be synthesized by standard conditions using the phosphoramidite method. Deprotection of the phosphate triester (39) can be accomplished by treatment with TMSBr. The oxymethyl phosphate prodrug 21 can be synthesized by initial formation of a methylthiomethyl ether (40) from MMB, followed by reaction of compound 40 with phosphoric acid in the presence of NCl, and then treatment with $Na_2CO_3$.
Figure 11:
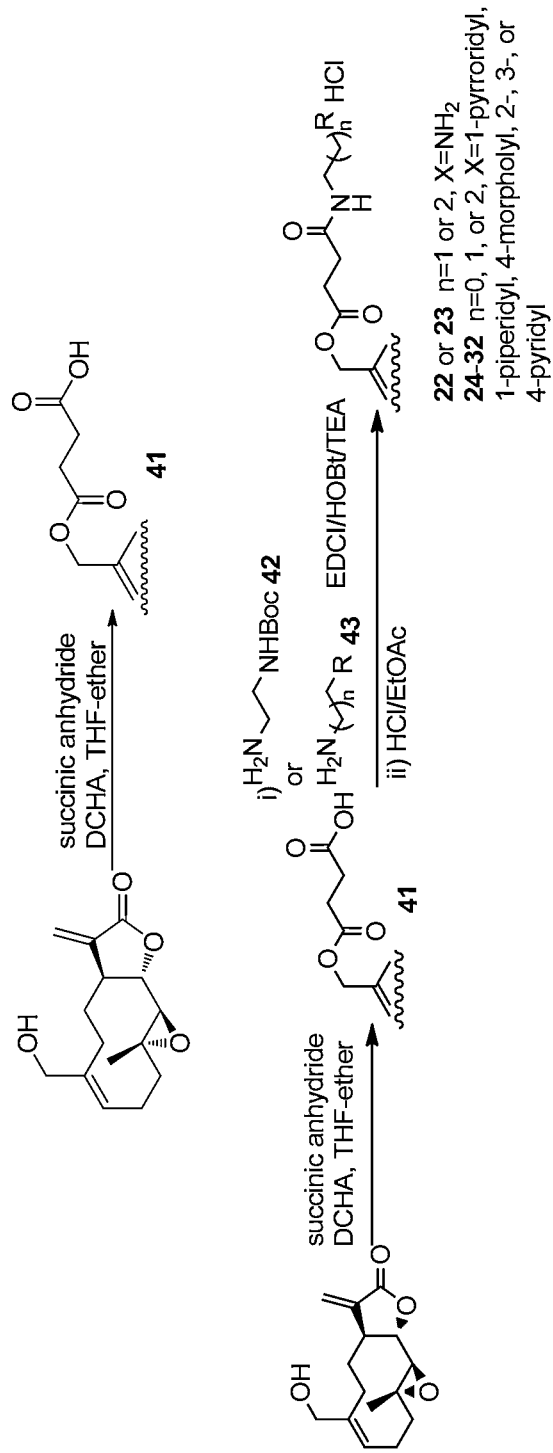
FIG. 11 shows synthesis of prodrugs 22-32 from FIG. 8. Prodrugs 22-32 can be synthesized by initial treatment of MMB with succinic anhydride in the presence of dicyclohexylamine (DCHA) to form hemisuccinate 41, followed by coupling of 41 with amine 42 or 43 utilizing the EDCI-HOBt coupling method, and deprotection (for 22 and 23).

The syntheses of the prodrugs shown in FIG. 8 are outlined in FIGS. 9-11. Compounds I-10 can be synthesized by Steglich esterification of MMB with an appropriate amino group protected AA to afford compound 34, followed by deprotection (FIG. 9B). Alternatively, as we have determined in the synthesis of biotinylated MMB (Irfan et al., 2010), a Mitsunobu reaction could also be used to form the ester group in 34. The requisite Boc-protected AAs for prodrugs 1-10 can be obtained from commercial sources. For the Lys-containing prodrug 9, both amino groups need to be protected. Reaction of MMB with an appropriate Boc-AA chloromethyl ester 35 will afford compound 36, which upon deprotection will furnish prodrugs 11-13 (FIG. 9B). Compound 35 can be prepared from Boc-AA and chlorobromomethane (Gomes et al., 2003).

Carbamate prodrugs 14-17 and carbonate prodrug 18 and 19 can be prepared from the substitution reaction between mono-Boc protected diamine or N-Boc aminopropanol (38) and 4-nitrophenyl MMB carbonate (37), followed by deprotection. This procedure has been utilized extensively in our laboratories. Compound 37 can be prepared by reacting MMB with 4-phenyl chloroformate (FIG. 10A).

Phosphate prodrug 20 can be synthesized by standard conditions using the phosphoramidite method. Deprotection of the phosphate triester (39) can be accomplished by treatment with TMSBr (DeGoey et al., 2009; Fu et al., 2009) (Scheme 3). The oxymethyl phosphate prodrug 21 can be synthesized by initial formation of a methylthiomethyl ether (40) from MMB, followed by reaction of 40 with phosphoric acid in the presence of NCl, and then treatment with $Na_2CO_3$ (DeGoey et al., 2009) (FIG. 10B).

Prodrugs 22 and 32 can be synthesized by initial treatment of MMB with succinic anhydride in the presence of dicyclohexylamine (DCHA) to form hemisuccinate 41, followed by coupling of 41 with amine 42 and 43 utilizing the EDCI- HOBt coupling method, and deprotection (for 22 and 23) (Sohma et al., 2003) (FIG. 11).

The Boc protective group used in FIGS. 9B, 10A and 11 can alternatively be interchanged for other protective groups, such as Fmoc, if the de-Boc reaction is problematic. The Boc protecting group, t-butyloxycarbonyl, is used as a typical amine protecting group. Fmoc, fluorenylmethyloxycarbonyl, is also used as an amine protecting group. In certain aspects, the final products, except for the phosphates 20 and 21, will be converted into salt forms to prevent possible inter- or intra-molecular Michael addition, and in some cases, self-cleavage of the pro-moiety.

The number of prodrugs can be easily expanded by utilizing the same synthetic methodology as in Schemes 1, 2, and 4. For example, in one aspect, various hydroxy alkyl ester derivatives of MMB can be synthesized. For example, MMB hydroxyacetate ester; MMB 3-hydroxy-2,2-dimethylpropionate ester; MMB 3-hydroxy-2-hydroxymethylpropionate ester; and MMB 2,2-bis-(hydroxymethyl)propionate ester can be synthesized as described in U.S. Pat. No. 5,362,718, which is incorporated herein by reference. MMB derivatives having the ester group —CO($CR^3R^4$)$_b$ ($CR^5R^6$)$_d$ ($CR^7R^8R^9$)$_e$; wherein $R^3$ and $R^4$ are each, independently, hydrogen, alkyl of 1-6 carbon atoms, trifluoromethyl, or —F; $R^5$ and $R^6$ are each, independently, hydrogen, alkyl of 1-6 carbon atoms, —($CR^3R^4$)$_f$$OR^{10}$, —$CF_3$, —F, or —$CO_2R^{11}$, or R5 and R6 may be taken together to form X or a cycloalkyl ring of 3-8 carbon atoms that is optionally mono-, di-, or tri-substituted with —($CR^3R^4$)$_f$$OR^{10}$; $R^7$ is hydrogen, alkyl of 1-6 carbon atoms, —($CR^3R^4$)$_f$$OR^{10}$, —$CF_3$, —F, or —$CO_2R^{11}$; $R^8$ and $R^9$ are each, independently, hydrogen, alkyl of 1-6 carbon atoms, —($CR^3R^4$)$_f$$OR^{10}$, —$CF_3$, —F, or —$CO_2R^{11}$; or R8 and R9 may be taken together to form X or a cycloalkyl ring of 3-8 carbon atoms that is optionally mono-, di-, or tri-substituted with —($CR^3R^4$)$_f$$OR^{10}$; R10 is hydrogen, alkyl of 1-6 carbon atoms, triphenylmethyl, benzyl, alkoxymethyl of 2-7 carbon atoms; R11 is hydrogen, alkyl of 1-6 carbon atoms; X is 5-(2,2-di-(alkyl of 1-6 carbon atoms))[1,3]dioxanyl, 5-(2,2-di-(cycloalkyl of 3-8 carbon atoms))[1,3]dioxanyl, 4-(2,2-di-(alkyl of 1-6 carbon atoms))[1, 3]dioxanyl, 4-(2,2-di-(cycloalkyl of 3-8 carbon atoms))[1,3]dioxanyl, 4-(2,2-di-(alkyl of 1-6 carbon atoms))[1,3]dioxalanyl, or 4-(2,2-di-(cycloalkyl of 3-8 carbon atoms))[1,3]dioxalanyl; b=0-6; and f=0-6 at the 14-OH position can be prepared by acylation of MMB using protected hydroxy and polyhydroxy acids, alkoxy or polyalkoxy carboxylic acids that have been activated, followed by removal of the alcohol protecting groups, if so desired. Several procedures for carboxylate activation are known in the art, but the preferred methods utilize carbodiimides, mixed anhydrides, or acid chlorides. For example, an appropriately substituted carboxylic acid can be activated as a mixed anhydride, with an acylating group such as 2,4,6-trichlorobenzoyl chloride. Treatment of MMB with the mixed anhydride under mildly basic condition provides the desired compounds. Alternatively, the acylation reaction can be accomplished with 1-(3-dimethylaminopropyl)-3-ethylcarbodiimide hydrochloride and dimethylaminopyridine. For example, 2,2-bis(hydroxymethyl)propionic acid isopropylidene ketal can be prepared according to the procedure of Bruice, J. Am. Chem. Soc. 89:3568 (1967)) and treated with triethylamine in anhydrous THF at 0° C. under nitrogen and 2,4,6-trichlorobenzoyl chloride added. The MMB can be added to the mixed anhydride under mildly basic conditions; e.g., DMAP, and the isopropylidine ketal protection can be removed by treatment with, e.g., 1 N HCl/THF.

In one aspect, the salt of the MMB derivative is a pharmaceutically acceptable salt. In various aspects, the pharmaceutically acceptable salt is selected from the tosylate, methanesulfonate, acetate, citrate, malonate, fumarate, tartarate, succinate, benzoate, ascorbate, α-ketoglutarate, and α-glycerophosphate salts of the MMB derivative. Suitable inorganic salts may also be formed, including hydrochloride, sulfate, nitrate, bicarbonate, and carbonate salts. In one aspect, the HCl salt will be utilized. In another aspect, the fumarate salt will be utilized.

Prodrug Stability Under Physiological Conditions

Prodrugs encounter a wide range of pH when administered orally to patients. Oral dosing exposes compounds to pH 1 to 2 in the stomach, pH 4.5 at the beginning of the small intestine, pH 6.6 as an average pH for the small intestine, and pH 5 to 9 in the colon. The mean fasting stomach pH of an adult is approximately 2, and increases to 4-5 following ingestion of food. These are useful pHs for in vitro evaluation of the chemical stability of a prodrug candidate.

Important insights can be obtained from incubating the prodrug with simulated GI fluids in vitro. These include simulated gastric fluid (SGF) and simulated intestinal fluid (SIF). These materials are specified in the United States Pharmacopeia (USP). The SGF components are pepsin (an acidic protease enzyme), NaCl and pH 1.2 (adjusted with HCl). SGF simulates stomach fluid and incorporates acidic and enzymatic hydrolysis conditions. The SIF components are pancreatin (mixture of amylase, lipase and protease enzymes from hog pancreas), and monobasic phosphate buffer with pH adjustment to 6.8 using NaOH. SIF mimics the pH and hydrolytic enzymes of the intestine. The main purpose of these assays is to predict prodrug stability in the GI tract after oral dosing. The data obtained can be helpful in structural optimization of prodrug entities to improve GI stability and enhance bioavailability, and for prioritizing compounds for subsequent in vivo studies.

Blood contains a large number of hydrolytic enzymes such as cholinesterase, aldolase, lipase, dehydropeptidase, and alkaline and acid phosphatase. If the prodrug has affinity for one of these enzymes and it has a hydrolyzable group in the right position, it can be efficiently cleaved in the plasma to afford the parent drug. Prodrugs are often utilized to improve absorption from the gastrointestinal tract, since the prodrug will be designed to enhance GI absorption by improvement in physicochemical properties compared to the parent drug. Once in the plasma, the prodrug is designed to be rapidly hydrolysed to afford the parent drug. Therefore, before in vivo prodrug studies in mice are performed, plasma stability data must be generated to determine if the prodrug is stable in the GI tract (Kern and Di, 2008).

Thus, with the aim of improving the oral bioavailability of the parent drug, MMB, all prodrug entities synthesized will initially be evaluated for physiological stability in buffers ranging from pH 1 to pH 9, as well as in SGF, SIF and in mouse plasma. The following experiments will be performed to determine stability in the GI tract and susceptibility td enzymatic hydrolysis to the parent drug in plasma:

pH: Stability in aqueous buffers (37° C., pH 1-9)
 GI: Stability in simulated gastric fluid (USP, 37° C.)
 GI: Stability in simulated intestinal fluid (USP, 37° C.)
 Plasma: Stability in mouse plasma (37° C.)

Specific experimental stability protocols are shown in the Examples.

Chemical Probes

One embodiment provides chemical probes based on 3 that retain antileukemic activity, but contain a "reporter" or a marker that could serve to highlight the subcellular localization or biochemical interactions of the probe. In one aspect, the MMB conjugates of the disclosure are utilized as laboratory tools. In one aspect, a labeled MMB conjugate is used to identify MMB target proteins in AML cells. In another aspect, a labeled MMB conjugate is used for delineating the cellular proteins and signaling cascades influenced by 3 or its analogs.

In one specific aspect, the disclosure provides MMB derivatives conjugated to a biotin moiety that can be used to investigate interactions of MMB (3) with cellular proteins, as well as to study its localization into organelles through microscopy. In a specific aspect, the disclosure provides a chemical route for synthesis of a biotinylated analog of 3 via conjugation of the allylic hydroxyl group. In another specific aspect, the MMB conjugate compound 4 is shown to be a robust agent for the identification of protein binding events. The utilization of this probe presented an opportunity to identify all proteins directly modified by 3, and thereby reveal other mechanisms contributing to anti-leukemic activity of MMB.

The synthesis of biotinylated MMB, 4, utilized PTL as starting material, via selenium oxide oxidation of the allylic methyl group applying a modification of the method of Macias et al., *Phytochemistry*, 1992, 31, 969. The allylic methyl group of PTL was subjected to SeO$_2$/t-BuOOH oxidation, yielding a mixture of MMB (3) and aldehyde 5. This reaction proved to be particularly fickle, with the aldehyde 5 being the major side-product that formed in significant quantities and impaired chromatographic isolation of 3. There was a significant variation in the quantity of 5 formed in relation to 3. For optimal oxidation of 1 to MMB (3), the literature procedure prescribes a combination of SeO$_2$ and t-Butyl hydroperoxide, which in our hands afforded a mixture of the required alcohol 3 and the aldehyde 5 in approximately a 1:1 ratio. While the quality of t-butyl hydroperoxide was inconsequential to the ratio, the quality (purity) of SeO$_2$ was found to be very important. Samples that possessed the characteristic pink color of selenium were found to afford higher quantities of 5, at the expense of 3. In addition, alcohol 3 could only be separated from 5 with difficultly by silica gel chromatography. NMR spectroscopic analysis was consistent with the structural assignments reported by Macias et al., and an x-ray crystal structure obtained in our hands was identical to that previously reported by Gonzalez et al., *Tetrahedron*, 1988, 44, 4585.

A Mitsunobu reaction on 3 with Fmoc protected 12-aminododecanoic acid afforded 6. While the use of morpholine/piperidine is common for Fmoc deprotections, this transformation had to be carried out with TBAF instead, due to the possibility of morpholine/piperidine adding to the enone function of 6. The amine 7, formed in-situ, was treated directly with the pentafluorophenyl ester of biotin to afford the target compound 4. Purification of this reaction mixture proved to be challenging, with the best conditions being the elution of the evaporated reaction mixture from an Et$_3$N-treated silica column with a gradient of i-PrOH in CH$_2$Cl$_2$. It should also be noted that the germacrenolide ring of 3 seemed to be susceptible to the basicitiy of F— from TBAF, with numerous by-products being formed that lacked the Fmoc dodecanoic acid-biotin appendage, according to NMR spectral data. The identity of these by-products was not determined. The use of other coupling reagents, i.e. HATU and EDC, afforded reaction mixtures that could not be resolved on silica so as to afford 4 in an analytically pure form.

In one aspect, other biotinylated reagents can be prepared with a similar route of synthesis. In this aspect, a labeled biotin of the structure (II) can be prepared with, for example, various commercially available biotin reagents. In this aspect, p is 1-12 and q is 1-3.

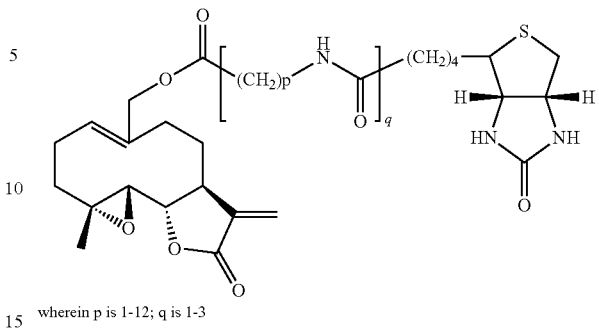

wherein p is 1-12; q is 1-3

Antileukemic Properties of Compound 4

Figure 3:
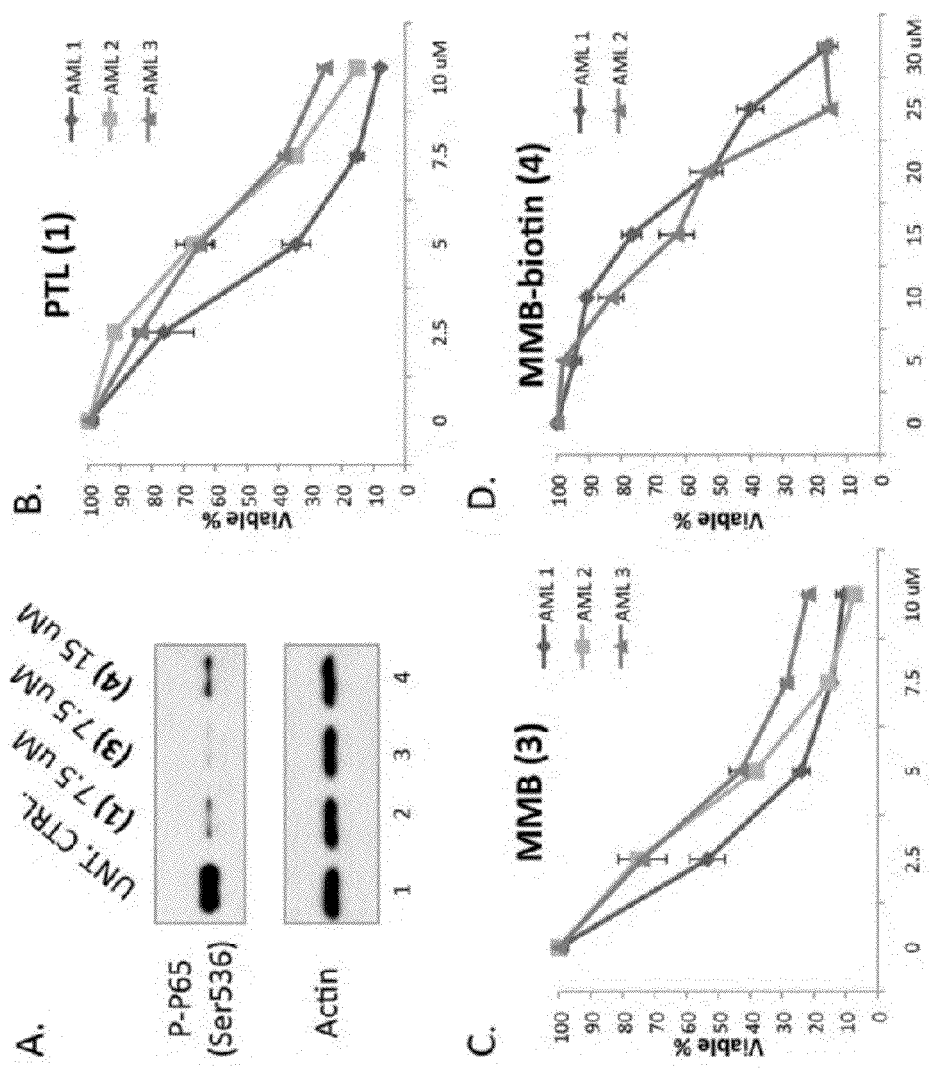
FIG. 3 shows biological activities of 4 compared to 1 and 3.

To validate the retention of functional properties, the activity of compounds 3 and 4 were compared to 1 using assays that measure inhibition of NF-κB activity. Primary leukemia cells were treated with varying concentrations of 1, 3 or 4 for six hours, followed by lysis and analysis by immunoblot. Inhibition of NF-κB activity was assessed by measuring phosphorylation of the NF-κB p65 subunit at Ser-536. As shown in FIG. 3A, a significant loss of phosphorylation is observed for 3 at 7.5 μM concentration, and for 4 at 20 μM concentration. To further evaluate the cytotoxicity of 3 and 4, cell viability was measured following 24 h exposure to each compound. As shown in FIG. 3B, efficient induction of cell death is achieved at 7.5 μM 3. To achieve a similar degree of cell death with 4, treatment at 20-30 μM was required, in good agreement with the NF-κB phosphorylation analysis shown in FIG. 3A. Thus, while 3 and 4 retain the biological properties of 1, the activity of 4 is reduced approximately 2-fold. The minor loss in activity might be attributed to steric hindrance resulting from the addition of the bulky biotin moiety.

The activities of 1 and 3 were compared. Allylic alcohol 3 was found to possess potency and selectivity similar to 1. Thus, MMB is active in spite of being a melampolide and not a germacrenolide.

Figure 4:
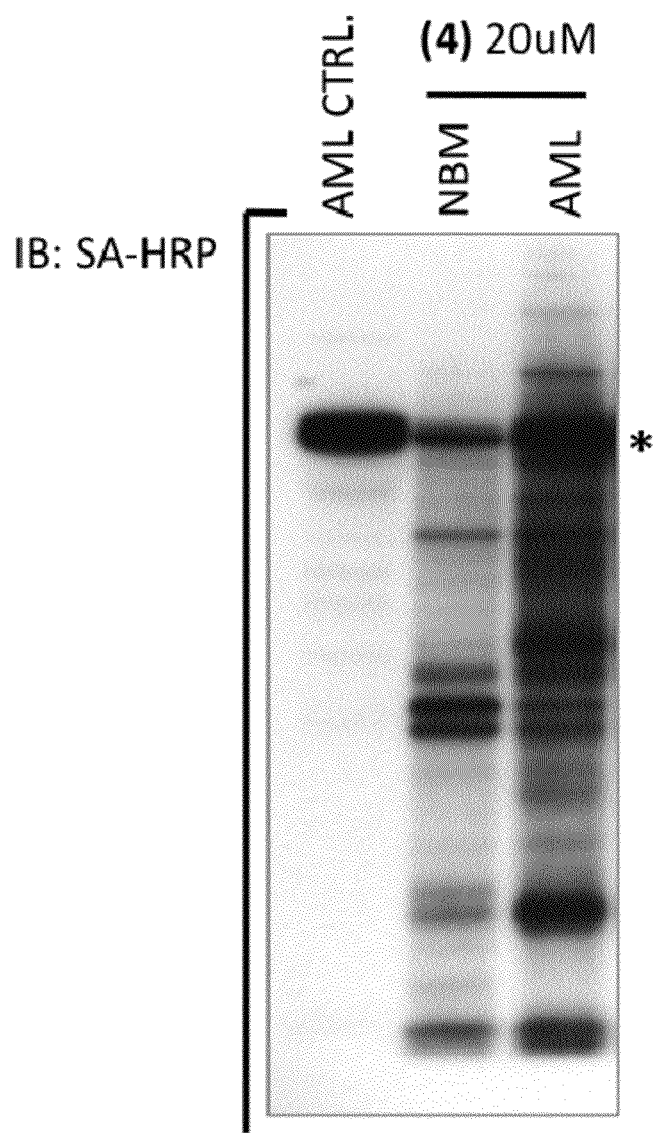
FIG. 4 shows binding of targets of 4 in NBM and AML samples in an immunoblot analysis using a streptavidin probe. The asterisk* marks a non-specific band recognized by SA-HRP probe. Whole cell lysates from normal bone marrow (NBM) in lane 2 is shown in comparison to acute myeloid leukemia (AML) cells in lane 3. An identical protein/compound 4 ratio was used for NBM and AML preparations.
Figure 5:
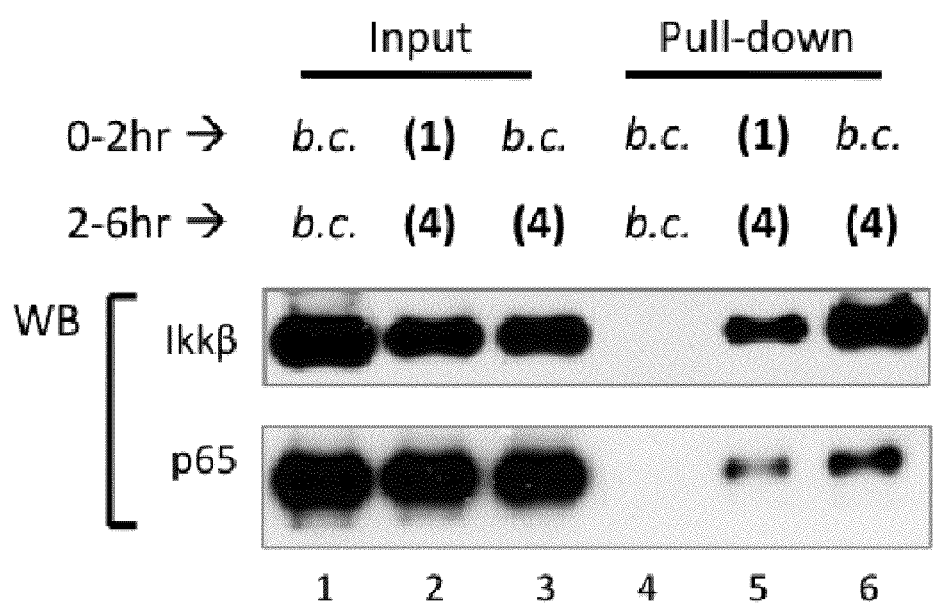
FIG. 5 shows Western blot of primary leukemia cells that were pretreated for 2 h with compound 1 (lanes 2, 5) or biotin control (b.c.) (lanes 3,6), prior to a 4 h incubation with compound 4. Cells were then lysed and immuno-precipitated by streptavidin beads. Pulldown products were analyzed by immunoblot to identify specific proteins. One product identified was IKK-β, the known target of compound 1; also the NF-kB p65 subunit was identified as a direct target in the pull-down. Preincubation with compound 1 potently reduced binding of IKK-β or p65 to compound 4 (lane 5), indicating such binding between IKK-β or p65 and compound 4 is through the same mechanism between IKK-β or p65 and compound 1.

Subsequent studies employed 4 as a reagent to identify potential leukemic proteins modified by MMB. Primary human cells were treated with 20 uM 4 for 6 h, followed by lysis and immunoblot analysis using a streptavidin probe. As shown in FIG. 4, multiple protein targets were identified in the whole cell lysates. Notably, the analysis of normal bone marrow (NBM) cells (lane 2) in comparison to acute myeloid leukemia (AML) cells (lane 3) indicates distinct differences in the spectrum of cellular targets, even though the identical protein-compound 4 ratio is used for normal and leukemic preparations (*marks a non-specific band recognized by SA-HRP probe). Thus, while the chemistry of 4 should be essentially the same in any cell type, there must be intrinsic differences between normal and leukemic cells that lead to the interaction with unique targets. We propose that this differential binding contributes to the leukemia-specific cell death previously described for 1. To further validate the utility of 4 for analysis of protein targets, we performed biochemical pulldown studies. Previous studies have demonstrated that biotinylated 1 binds to the NF-kB regulatory protein IKK-β. Kwok et al. *Chem. Bio.*, 2001, 8, 759. Therefore, we tested whether 4 would also bind this protein. In FIG. 5, primary leukemia cells were pretreated for 2 h with 1 (lanes 2, 5) or biotin control (b.c.) (lanes 3, 6), prior to a 4 h incubation with 4. Cells were then lysed and immuno-precipitated by streptavidin beads. Pulldown products were analyzed by immunoblot to identify specific proteins. As shown in FIG. 5, one product identified was IKK-β, the known target of 1, thereby validating the specificity of the reagent for targets relevant to the anti-leukemia mechanism of action. Kwok et al., *Chem. Bio.,* 2001, 8, 759; Hehner et al., *J. Immunol.* 1999, 163, 5617.

In addition, the NF-kB p65 subunit was identified as a direct target in the pull-down, suggesting interactions with multiple components of the NF-kB signaling pathway. Notably, preincubation with 1 potently reduced binding of IKK-β or p65 to 4 (lane 5), indicating such binding between IKK-β or p65 and 4 is through the same mechanism between IKK-β or p65 and 1.

Taken together, these data show that malampomagnolide B is a new antileukemic agent with remarkable selectivity for leukemic cells over normal hematopoietic cells. This selectivity is derived from its unique ability to exploit biochemical differences between the two cell types. In one aspect, the biotin conjugate 4 is utilized for the identification of protein binding targets of both MMB 3 and PTL 1.

Biological Efficacy Studies

Each candidate compound is subjected to a comprehensive set of analyses to establish biological efficacy. Those compounds that most effectively eradicate primary human AML cells, including LSC, while not harming normal hematopoietic stem and progenitor cells will be considered the highest priority for further development. Biologically efficacy will be determined using the experimental methods outlined below. For each assay, a panel of 10 primary human AML specimens and normal bone marrow specimens are employed for initial screening, with follow up using additional specimens as needed to attain statistical significance for any particular readout.

Xenograft Studies:

Xenografts using primary human hematopoietic cells transplanted into the NOD/SCID gamma-chain deficient (NSG) strain are now widely considered the "gold standard" for in vivo modeling of normal hematopoiesis and leukemia (Pearson et al., 2008). Not only does this approach allow direct analysis of primary tissue, it is also quite useful in characterizing the consequences of treatment on LSCs. Thus, all studies on biological efficacy will utilize this model. Two strategies will be employed for analysis of compounds. First, primary human AML vs. normal specimens will be treated with compounds of interest for 24-48 hours in ex vivo culture, followed by transplantation (intravenous) into sublethally irradiated NSG mice. At 6-8 weeks post-transplant, animals will be sacrificed and bone marrow cells will be isolated to assess the percentage of human cells present. Because engraftment in NSG mice is directly proportional to LSC content, this assay provides a quantitative measure of direct LSC targeting. Second, primary AML vs. normal specimens will be transplanted into NSG mice as outlined above. Following 4-6 weeks to permit engraftment of human cells, animals will be treated with varying doses and schedules of our lead compound to assess in vivo efficacy and specificity. Again, analysis of human cells in bone marrow will be used to readout in vivo activity. For studies where efficacy is obtained, secondary limiting-dilution NSG transplantation will be performed to quantify effects on the LSC population.

Flow Cytometry:

In addition to simply analyzing total leukemic cell burden in the xenograft studies above, detailed cytological analyses using flow cytometry will be employed. Following treatment of xenograft-bearing mice, bone marrow cells will be isolated and subjected to several forms of analysis. Studies will be conducted to assess cell death (i.e. apoptotic frequency), differentiation, and cell cycle status using well established flow cytometry methods. Briefly, specimens will be labeled with cell surface antibodies that identify normal and leukemic stem and progenitor cell populations (e.g. CD34, CD38, CD123, CD33, and CD96). To assess cell death, specimens will also be labeled with Annexin V as an indicator of apoptosis, or using flow cytometry TUNEL protocols to measure DNA breaks. Together, these two methods will provide a quantitative, measure of cell death within phenotypically defined subpopulations. To assess induction of differentiation, cell surface phenotype will be compared before and after treatment with candidate prodrugs. Loss of antigens associated with a primitive phenotype, and/or increased expression of markers associated with myeloid differentiation (e.g. CD11b, CD14, CD16, CD66b, etc) will be evaluated. To assess changes in cell cycle status, at varying times of exposure to candidate compounds, cells will be labeled with the antibodies noted above, followed by fixation/permeabilization and nuclear labeling with anti-Ki67 antibody. These studies will determine whether candidate prodrugs reduce or arrest growth in the absence of overt cytotoxicity. Moreover, by comparing AML specimens to normal controls, we will ascertain the resultant specificity of each prodrug.

Colony-Formation Assays:

In parallel to the flow cytometry studies outlined above, AML versus normal cells isolated from xenograft-bearing mice will also be evaluated using in vitro colony-formation assays. Briefly, before and after treatment with prodrugs of interest, 10-50,000 cells isolated from bone marrow will be plated in methylcellulose media supplemented with standard cytokines (human specific). After 10-14 days of incubation, human colony-formation will be scored for blast, myeloid, or lymphoid morphologies. This assay directly measures the effect of drug treatment on the progenitor cell population.

Biological Efficacy Studies:

All studies in this application will employ primary human AML cells as a means to capture the most authentic possible results. A large collection of primary AML specimens (over 200) will be employed for the proposed studies. A series of in vivo biological assays will be performed to evaluate the efficacy and specificity of candidate compounds using the methods of Howard et al., Genetic manipulation of primitive leukemic and normal hematopoietic cells using a novel method of adenovirus-mediated gene transfer. *Leukemia,* 13:1608-1616, 1999; Jordan et al. The interleukin-3 receptor alpha chain is a unique marker for human acute myelogenous leukemia stem cells. *Leukemia,* 14:1777-1784, 2000; Guzman et al., Nuclear factor-kappaB is constitutively activated in primitive human acute myelogenous leukemia cells. *Blood,* 98:2301-2307, 2001; Guzman et al., The sesquiterpene lactone parthenolide induces apoptosis of human acute myelogenous leukemia stem and progenitor cells. *Blood,* 105:4163-4169, 2005; Guzman et al., An orally bioavailable parthenolide analog selectively eradicates acute myelogenous leukemia stem and progenitor cells. *Blood,* 110:4427-4435, 2007; and Hassane et al., Discovery of agents that eradicate leukemia stem cells using an in silico screen of public gene expression data. Blood, 111:5654-5662, 2008; each of which is incorporated by reference.

Molecular Mechanisms Controlling Cell Death Induced by Parthenolide-Based Drugs.

A variety of studies have been performed to better understand the mechanism of action of parthenolide-based drugs. These studies fall into the following three major categories:

Genomic Analyses:

gene expression profiling was performed on 14 primary AML specimens, with or without PTL treatment as a means for understanding the global consequences of drug treatment.

These data are publicly available (accession #: GSE7538) and have been previously described (Hassane, Guzman et al. 2008). Briefly, we found that genes up-regulated by PTL treatment fall almost exclusively into the category of stress response factors. Specifically, strong induction of all major components of the heat shock protein (HSP) family are readily evident, as are the anti-oxidant defenses (Nrf2/HMOX1 pathway), endoplasmic reticulum (ER) stress (GRP87), and mediators of thioredoxin and glutathione activity, including TXNIP, SLC7A11, SLC3A2, and GCLM. Taken together, the response indicates that PTL mediates a strong induction of oxidative stress, a finding consistent with previous reports (Zhang et al., 2004). Genes down-regulated by PTL are more heterogeneous in terms of biological function, but include downstream targets of NF-kB, as well as genes implicated in control of differentiation. The most prevalent pathway modulated is NF-kB. Preliminary findings for MMB indicate a similar pattern of gene expression changes.

Figure 6:
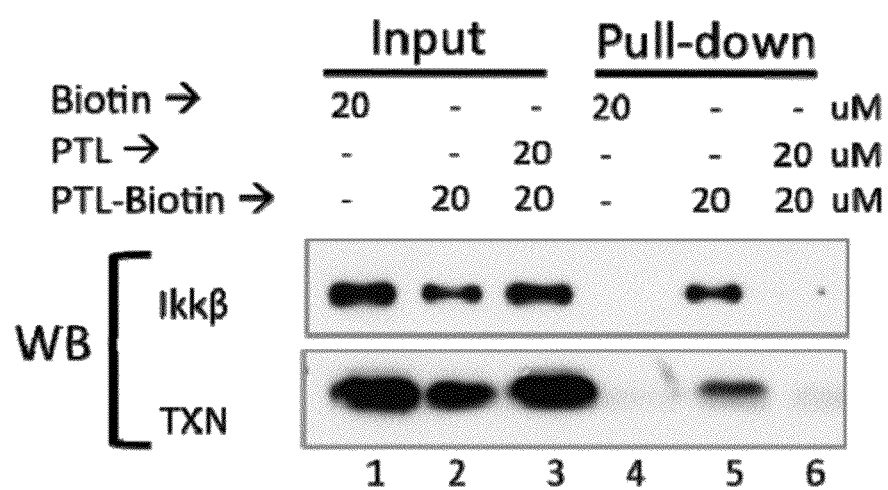
FIG. 6 shows another Western blot analysis of AML cells using compound 4, with and without treatment with compound 1. Primary AML cells were treated with PTL-biotin for 6 hours followed by lysis and biochemical pull-downs using streptavidin coated agarose beads. Controls include cells incubated with biotin alone, or preincubated with native PTL prior to the addition of PTL-biotin. (i.e. competitive binding studies). Lysates were analyzed by Western blot (WB) for the presence of IKK or thioredoxin. (TXN). Lanes 1-3 labeled "input" represent whole cell lysates for each condition. Lanes 4-6, labeled "pull-down" are the material bound to streptavidin beads. No pull down is observed with biotin alone (lane 4). Both proteins are bound by PTL-biotin (lane 5). Preincubation with PTL competes the PTL-biotin interaction (lane 6).

Proteomic Studies:

To identify direct targets of MMB, the biotinylated MMB analog was employed for biochemical studies. Preliminary studies conducted with this compound indicate that it is a powerful tool in defining drug targets and underlying mechanisms of action. As shown in FIGS. 4-6, MMB-biotin can be used to detect proteins by Western blot, or to treat leukemia cells, followed by lysis and analysis of bound target proteins. As expected, the spectrum of targets is relatively broad. Interestingly, the targets differ somewhat between normal and AML cells, suggesting some elements of drug selectively may be related to a difference in protein targets in the two cell types. In one aspect, the labeled MMB compound, such as a biotinylated MMB compound 4, can be used to determine the relative difference between AML cells and normal cells. Pull-down products have been analyzed by tandem HPLC-MS, and the proteins and families summarized in Table 2 have been confirmed as direct targets of MMB-biotin.

TABLE 2

| PTL Targets identified by mass spec and/or immunoblot |
|---|
| Metabolic Pathways |
| Pyruvate kinase isozymes M1/M2 (PKM2)<br>Aldo-keto reductase family 1, member B1 (ALDR1) |
| Heat Shock Responses |
| Chaperone (HSP60)<br>90 kDa heat shock protein<br>70 kDa heat shock protein |
| Redox State |
| Gltathione-S-transferase P1 (GSTP1)<br>Microsomal glutathione-S-transferase 3 (MGST3)<br>Thioredoxin (TRX1) |
| NF-kB signaling |
| I kappa kinase beta subunit (IKK-beta)<br>NF-kB p65 subunit |

Without being bound by theory, several of the targets involve proteins that regulate the defense mechanisms up-regulated by PTL treatment (as determined by the genomic analyses above). For example, both thioredoxin and glutathione-S-transferase are targets of MMB. In addition, metabolomic studies indicate that glutathione is profoundly suppressed by PTL (11.2-fold reduction), a finding almost certainly true for MMB as well. These data indicate potentially severe impairment of the mechanism required to manage oxidative stress. Furthermore, MMB also directly binds the major components of the HSP family (HSP60, 70, and 90). Computational modeling indicates that binding of MMB would likely occur via cysteine 17, a residue at the center of the ATP binding pocket for HSP70 (data not shown). If true, then MMB could also impair the function of one or more HSPs. Taken together with the genomic data, these findings indicate a unique mechanism of action, where agents of this class act by inducing multiple stress response mechanisms and simultaneously impairing those very same mechanisms from functioning properly.

The data extend previous reports on PTL mechanism, by showing that inhibition of NF-kB occurs through direct binding of both the p65 subunit, as well as the NF-kB regulator IKK-beta (Table 2). It was previously demonstrated that the NF-kB pathway is constitutively active in primary human AML cells, but not naïve normal hematopoietic cells. (Guzman et al., 2001). The data also indicate a significant role for NF-kB in the viability and response to chemotherapy for AML cells. Indeed, as a critical regulator of survival in many types of cancer, it appears likely that NF-kB has a similar function in AML cells, and its inhibition should sensitize leukemic cells to death. Again, without being bound by theory, our finding that PTL is a strong NF-kB inhibitor in AML cells implies that an important component of the MMB mechanism may also involve inhibition of NF-kB.

Figure 7:
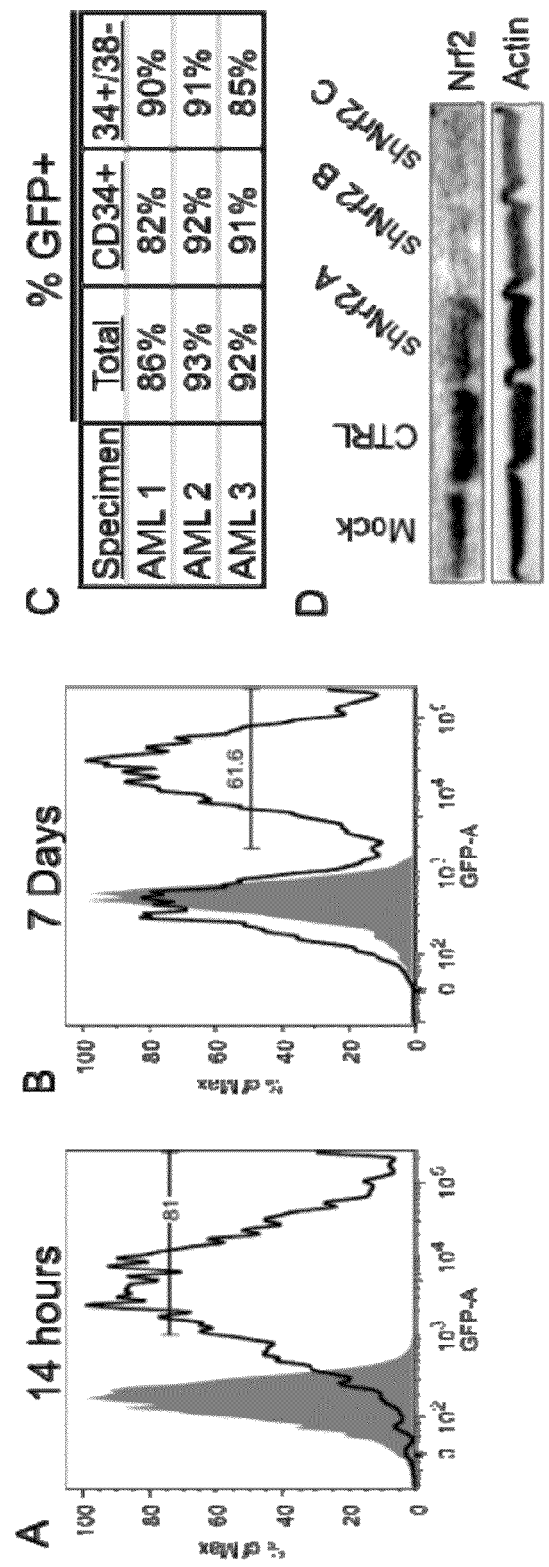
FIG. 7 shows efficiency of gene transfer for primary AML specimens. Green fluorescent protein (GFP) has been widely used as a lineage marker for mammalian cells. The use of fluorescent proteins allows cells to be tracked during manipulation. Primary AML cells exposed to a concentrated lentivirus encoding GFP for 6 hours. Analysis 8 hours later (A) and at 7 days (B) post-infection. Primary AML specimens (C) were infected with lentivirus encoding GFP and analyzed after overnight culture. (D) Western blot showing efficacy of lentiviral expression of shRNA targeted to the Nrf2 mRNA.

Molecular Genetic Tools for Analysis of Primary AML Cells:

For further studies regarding MMB mechanism of action, it will be critical to perform efficient gene transfer into primary AML and normal populations. To this end, we have optimized lentiviral-vector mediated systems and demonstrated effective gene transfer and functional manipulation of primary AML cells. Briefly, virus producing cells (293TN) are transfected with the vector of interest using a calcium phosphate based protocol that routinely achieves 90% or greater transfection efficiency. Virus-containing supernatant is harvested 24-48 hours later, and is then subjected to a PEG-mediated precipitation procedure, which pulls down viral particles (Kutner et al., 2009). We typically achieve over 200-fold concentration of virus using this method. Thus, by combining high efficiency transfection of virus-producing cells, with PEG precipitation, we are able to generate very high titer viral stocks. As shown in FIG. 7, viral stocks prepared by this method are highly competent to infect primary AML cells. Remarkably, this very efficient infection is achieved with only a single exposure to virus for 6 hours, with gene transfer efficiency first measured 8 hours later (FIG. 7A). Notably, the high efficiency shown for the early timepoint in FIG. 7A could be influenced by some degree of so-called "pseudo-infection" (i.e. binding of free GFP protein rather than true gene transfer). To investigate this issue, we simply cultured the cells for 7 days and re-tested GFP fluorescence. As shown in FIG. 7B, there is a slight reduction in the percentage of positive cells, but the GFP+ and GFP− populations are now clearly resolved and indicate that the cells still positive are true gene transfer events. Importantly, the infection efficiencies we observe are equally high in the primitive populations (FIG. 7C: CD34+ and CD34+/CD38−), suggesting the method is also useful for analysis of LSC. Subsequent transplantation of infected cells has demonstrated they are fully competent to engraft immune deficient mice (not shown). These data indicate that rapid and efficient gene transfer is entirely feasible for primary AML specimens, and will permit both short-term culture and long-term functional assays (e.g. colony-formation assays, xenograft analysis, etc.) to be performed. Further, as shown by the example in FIG. 7D, expression of shRNA constructs can be achieved to knock-down expression of genes of interest.

Molecular and Cellular Characterization of Melampomagnolide B

The mechanism of parthenolide-mediated cell death was previously studied in primary AML cells using a variety of methods. The data thus far indicate the PTL mediates leukemia-specific cell death by a mechanism that involves inhibition of NF-kB, inhibition of glycolysis, and induction of both oxidative and ER stress. Going forward, we propose to extend these studies to melampomagnolide B and to perform comparative studies between primary AML and normal specimens in order to identify those molecular properties that are uniquely perturbed in leukemia cells, thereby leading to leukemia-specific cell death. These studies will employ a comprehensive set of genomic, proteomic, and molecular genetic methods in order to create a detailed model of melampomagnolide B mediated cell death.

Gene Expression Analyses of MMB

Previous studies on PTL employed array-based gene expression profiling and provided a comprehensive analysis of pathways modulated by drug treatment. In the present proposal, we will extend these studies to include MMB. In another aspect, labeled MMB compounds such as biotinylated MMB can be used in gene expression analyses; for example, in comparative analysis of gene expression changes in normal hematopoietic cells. This line of investigation can help to further understand the mechanism by which MMB induces selective death of leukemia cells. In addition, biotinylated MMB can be used in analysis of enriched populations of LSC to determine gene expression changes that may occur specifically within this distinct subpopulation.

In one aspect of the disclosure, AML versus normal specimens are treated with MMB-biotin for varying times followed by isolation of RNA (mRNA and microRNA) for expression analysis. Previously, we have found that 6 hours of treatment is optimal for analysis of gene expression, as this captures a full spectrum of relatively early changes in gene expression, prior to the onset of overt cell death events. However, recent studies indicate that an earlier timepoint (approximately 1-2 hours) would also be useful. To determine the merit of additional timepoints, we will perform RT-PCR studies on a set of genes implicated in various pathways implicated in drug activity (e.g. NF-kB, HSPs, ER stress, oxidative stress, glycolysis, etc.) to determine the optimal timepoints for more detailed global analysis. With that data in place, each population of interest will be interrogated using RNA-seq (ABR SOLiD system) to a depth of at least 20 million reads to obtain a comprehensive gene expression profile of treated cells. These data will be analyzed to provide a detailed set of genes and pathways modulated by MMB. MMB labeled compounds, such as biotinylated MMB, will be a valuable laboratory tool to help define pathways differentially active between AML and normal cells, as well as between enriched LSC populations and bulk AML tumor cells.

Proteomic Analyses of MMB-biotin

In another aspect, labeled MMB compounds such as biotinylated MMB can be used in proteomic analyses. An initial set of studies using MMB-biotin reagent was performed to identify protein targets in AML cells after 6 hours of treatment. However, these studies were performed on whole cell extracts, and were limited to only AML cells. Going forward we propose to extend these studies in three ways. First, fractionation of MMB-biotin treated cells will be performed to enrich membrane, cytosolic, and nuclear protein fractions. This will provide a much higher resolution analysis of potential protein targets. Second, time-course studies will be performed to determine whether other/additional timepoints are warranted. Third, once conditions for analysis of AML cells are defined, a parallel set of studies will be performed in normal hematopoietic cells, so as to identify proteins differentially bound in normal versus malignant cells. Preliminary data indicates a clear difference in the abundance and size of MMB targets between normal and AML cells, and differentially targeted proteins may be particularly informative in defining the underlying mechanism of MMB leukemia-specific activity.

AML versus normal specimens will be treated with MMB-biotin for varying times (0.5 to 6 hours), followed by lysis and fractionation to obtain membrane, cytoplasmic, mitochondrial, and nuclear preparations. Each fraction will be subjected to analysis by 2-D gel electrophoresis to capture a broad profile of protein targets for each condition. Where appropriate, specific specimens will be analyzed by tandem HPLC-MS to directly identify protein targets. These studies will generate a comprehensive list of proteins directly bound by MMB. These data will be integrated with the gene expression studies, and the previous studies on MMB, to create a detailed model of the mechanism of action for MMB.

Pathway Identification and Validation

In another aspect, labeled MMB compounds such as biotinylated MMB can be used to further validate key pathways it is extremely useful to perform molecular genetic studies as a means to directly demonstrate the mechanisms implicated by genomic and proteomic analyses. To this end, we have optimized lentiviral gene transfer for primary AML cells, and demonstrated that introduction of shRNA or dominant negative alleles is entirely feasible (see preliminary data, FIG. 4). Similarly, over-expression studies of exogenous genes products can be easily performed with the same technology. Thus, we are ideally positioned to interrogate any pathway of interest with respect to its role in AML cell biology and/or response to drug challenge. For example, previous studies with PTL indicate a role for the NF-☐B pathway in survival of AML cells. Therefore, genetic down-regulation of the NF-☐B pathway should impair AML cells and sensitize to challenge with various agents. Similarly, induction of ER stress is implicated in the cell death mechanism of PTL as well as MMB. Genetic inhibition of ER stress pathways should therefore at least partially abrogate leukemia-specific cell death induced by such agents. Using the data obtained from the above studies, we will design and test vectors to further refine the molecular model of MMB-mediated cell death.

Determination of the Pharmacokinetic Profile of Lead Prodrug Entities

Single compound, or discrete dosing studies, will be carried out on prodrug candidates of MMB to determine their suitability for in vivo evaluation studies in an animal model of leukemia. It is likely that MMB prodrugs will be absorbed intact from the gastrointestinal tract and will be efficiently cleaved enzymatically in plasma to afford the parent drug. The presence and identification of metabolites of both the prodrug and the parent drug may also provide important information on the mechanism of action of this novel sesquiterpene, especially with regard to potential active metabolites, the identification of which may be of value in the selection of new structural entities for consideration in future structure-activity and optimization studies.

The time course of appearance of the parent drug in BALB/C male mice (20-25 g) following oral administration of prodrug will be performed. A complete PK profile for MMB generated from each orally administered prodrug candidate will be performed in jugular vein-catheterized mice to determine half-life ($t_{1/2}$), maximum plasma concentration ($C_{max}$), time to reach maximum plasma concentration ($t_{max}$), volume of distribution ($V_{ss}$), area under the plasma concentration versus time curve from time 0 to infinity ($AUC_{0-\infty}$), and bioavailability (F %), as well as other important PK parameters. Our experimental design will include a comprehensive time course of the appearance of the parent drug, MMB, and the corresponding prodrug in mouse plasma over a therapeutically relevant dose range after oral administration of prodrug.

For determining bioavailability and PK profile of the proposed prodrugs, plasma concentrations of parent drug for each dose of prodrug candidate will be determined by drawing blood samples (150 μL) from jugular vein-catheterized mice at 6 time points after oral administration; the parent drug will also be administered by iv injection in a separate experiment. A total of 28 mice per prodrug (3 oral doses×4 mice+2 donor mice/group and 4 mice+2 donor mice for a single iv dose of the parent drug; 4 control mice will also be needed). The donor mice are utilized to provide blood to replace the 150 uL of blood withdrawn at each timepoint in the oral and iv dosing experiments. Plasma samples will be analyzed by HPLC/MS/MS to provide the time course of appearance and the $t_{1/2}$ of MMB generated from the prodrug candidates. These results will be used to identify suitable prodrugs for subsequent evaluation in a mouse model of leukemia, and to determine dosing regimens in these evaluation studies. While it is anticipated that an oral dosage form will provide a successful and desirable delivery route for the candidate prodrugs, development of other delivery routes can be also be pursued as discussed herein.

The compounds described herein are useful for treating cancer. Cancers treatable by the present therapy include the solid and hematological tumors, such as prostate cancer, ovarian cancer, breast cancer, brain cancer and hepatic cancer, comprising administering to a mammal afflicted with said cancer an amount of MMB derivative effective to inhibit the viability of cancer cells of said mammal. The MMB derivative may be administered as primary therapy, or as adjunct therapy, either following local intervention (surgery, radiation, local chemotherapy) or in conjunction with at least one other chemotherapeutic agent discussed hereinabove, as well as the solid tumors disclosed in U.S. Pat. No. 5,514,555. Hematological cancers, such as the leukemias are disclosed in the Mayo Clinic Family Health Book, D. E. Larson, ed., William Morrow, N.Y. (1990) and include CLL, ALL, CML and the like. Compounds of the present invention may be used in bone marrow transplant procedure to treat bone marrow prior to reintroduction to the patient. In addition, the compounds of the present invention may be used as chemotherapy sensitizers or radiation therapy sensitizers. Accordingly, a patient, or cells, or tissues, derived from a cancer patient, are pre-treated with the compounds prior to standard chemotherapy or radiation therapy. The present invention contemplates that MMB may also be used in such methods.

Within another aspect of the disclosure, methods are provided for inhibiting angiogenesis in patients with non-tumorigenic, angiogenesis-dependent diseases, comprising administering a therapeutically effective amount of a composition comprising MMB or an MMB derivative to a patient with a non-tumorigenic angiogenesis-dependent disease, such that the formation of new blood vessels is inhibited. Within other aspects, methods are provided for inhibit reactive proliferation of endothelial cells or capillary formation in non-tumorigenic, angiogenesis-dependent diseases, such that the blood vessel is effectively occluded. Within one embodiment, the anti-angiogenic composition comprising MMB derivative is delivered to a blood vessel which is actively proliferating and nourishing a tumor.

In addition to tumors, numerous other non-tumorigenic angiogenesis-dependent diseases, which are characterized by the abnormal growth of blood vessels, may also be treated with the anti-angiogenic MMB derivative compositions, or anti-angiogenic factors of the present invention. Anti-angiogenic MMB derivative compositions of the present invention can block the stimulatory effects of angiogenesis promoters, reducing endothelial cell division, decreasing endothelial cell migration, and impairing the activity of the proteolytic enzymes secreted by the endothelium. Representative examples of such non-tumorigenic angiogenesis-dependent diseases include corneal neovascularization, hypertrophic scars and keloids, proliferative diabetic retinopathy, arteriovenous malformations, atherosclerotic plaques, delayed wound healing, hemophilic joints, nonunion fractures, Osler-Weber syndrome, psoriasis, pyogenic granuloma, scleroderma, trachoma, menorrhagia, retrolental fibroplasia and vascular adhesions. The pathology and treatment of these conditions is disclosed in detail in published PCT application PCT/CA94/00373 (WO 95/03036), at pages 26-36. Topical or directed local administration of the present compositions is often the preferred mode of administration of therapeutically effective amounts of MMB derivative, i.e., in depot or other controlled release forms.

The anti-angiogenic compositions of the disclosure may also be utilized in a variety of other manners. For example, they may be incorporated into surgical sutures in order to prevent stitch granulomas, implanted in the uterus (in the same manner as an IUD) for the treatment of menorrhagia or as a form of female birth control, administered as either a peritoneal lavage fluid or for peritoneal implantation in the treatment of endometriosis, attached to a monoclonal antibody directed against activated endothelial cells as a form of systemic chemotherapy, or utilized in diagnostic imaging when attached to a radioactively labelled monoclonal antibody which recognizes active endothelial cells. The magnitude of a prophylactic or therapeutic dose of MMB derivative, an analog thereof or a combination thereof, in the acute or chronic management of cancer, i.e., prostate or breast cancer, will vary with the stage of the cancer, such as the solid tumor to be treated, the chemotherapeutic agent(s) or other anticancer therapy used, and the route of administration. The dose, and perhaps the dose frequency, will also vary according to the age, body weight, and response of the individual patient. In general, the total daily dose range for MMB derivative and its analogs, for the conditions described herein, is from about 0.5 mg to about 2500 mg, in single or divided doses. Preferably, a daily dose range should be about 1 mg to about 100 mg, in single or divided doses, most preferably about 5-50 mg per day. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an effective amount" or "an effective sensitizing amount" are encompassed by the above-described dosage amounts and dose frequency schedule.

Any suitable route of administration may be employed for providing the patient with an effective dosage of MMB derivative (e.g., oral, sublingual, buccal, rectal, intravenous, epidural, intrethecal, subcutaneous, transcutaneous, intramuscular, intraperitoneal, intracutaneous, inhalation, transdermal, nasal spray, nasal gel or drop, and the like). While it is possible that, for use in therapy, MMB derivative or its analogs may be administered as the pure chemicals, as by inhalation of a fine powder via an insufflator, it is preferable to present the active ingredient as a pharmaceutical formulation. The invention thus further provides a pharmaceutical formulation comprising MMB derivative or an analog thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof, such as a human patient or domestic animal.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semisolid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the agent from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Certain formulations comprise nanoparticles comprising MMB or an MMB derivative and a carrier protein (such as albumin). There are a wide variety of suitable formulations of the nanoparticle composition (see, e.g., U.S. Pat. Nos. 5,916, 596; 6,096,331 and 7,758,891, each of which is incorporated by reference). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof. The polymer matrix can be coated onto, or used to form, a medical prosthesis, such as a stent, valve, shunt, graft, or the like.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

For topical administration to the eye, the compounds can be administered as drops, gels (U.S. Pat. No. 4,255,415), gums (see U.S. Pat. No. 4,136,177) or via a prolonged-release ocular insert.

The invention will now be described in greater detail by reference to the following non-limiting examples.

EXAMPLES

Example 1

Synthetic Procedures for the Synthesis of Compounds 3, 4 and 6

Biotin was purchased from AK Scientific, Inc, Mountain View, Calif. All other reagents and chemicals were purchased from Aldrich Chemical Co., Milwaukee, Wis. THF and diethyl ether were distilled over sodiumbenzophenone ketyl and stored under argon. All other solvents and chemicals were used as received. TLC analyses were run on Analtech Silica Gel GF® plates. Melting points were determined on a Fisher Scientific melting point apparatus and are uncorrected. NMR spectra were run on a Varian 300 MHz NMR spectrometer in CDCl3 and chemical shifts are reported in ppm relative to TMS as internal standard. Mass spectra were recorded on a JEO: JMS-700T MStation or on a Bruker Autoflex MALDI-TOF MS. DMF was either distilled over P2O5 immediately before use or the anhydrous grade from Aldrich® was used. Parthenolide was purchased from Aldrich (St. Louis, Mo.). CHN analysis was performed by Atlantic Micro Labs, and are within ±0.4% of theoretical values. The synthesis of compound 3 has been reported elsewhere 13, and its characterization data are in agreement with reported values.

Melampomagnolide B (3). MMB was synthesized utilizing a modification of the method of Macias et al. via selenium oxide oxidation of the C10 methyl group of PTL, which also results in concomitant conversion of the geometry of the C9-C10 double bond from trans to cis. Macias et al., *Phytochemistry*, 1992, 31, 969. A solution of 1 (250.0 mg, 1.0 mmol) in $CH_2Cl_2$ was treated with $SeO_2$ (111.0 mg, 1.0 mmol) and tert-butyl hydroperoxide (1 M in dodecane, 1 mL) and the mixture was refluxed gently for an hour, after which it was evaporated. The resulting semisolid was subjected to silica gel chromatography to afford 3 (132.0 mg, 50%). Hexane/acetone=85: 15); White crystals; MP 172-176° C.; $^1$H NMR (300 MHz, CDCl$_3$) δ 6.25 (app., J=10.0 Hz, 1H), 5.66 (app. t, J=6 Hz, 1H), 6.56 (app. d, J=10.0 Hz, 1H), 4.12 (q, J=12.6 Hz, 2H), 3.86 (t, J=9.6 Hz, 1H), 2.83 (m, 2H), 2.49-1.13 (m, 5H), 1.72092 (m, 2H), 1.56 (s, 3H) ppm. $^{13}$C NMR (75 MHz, CDCl$_3$) δ 169.5, 139.6, 138.9, 127.7, 120.3, 81.3, 66.1, 63.6, 60.3, 43.1, 37.1, 25.9, 24.2, 24.0, 18.3 ppm; EI-MS m/z: 264.

14-(N-fmoc-12-Aminododecanoxy)melampomagnolide B (6)

A solution of 3 (264 mg, 1 mmol), Fmoc dodecanoic acid (437 mg, 1 mmol) and Ph3P (262 mg, 1 mmol) in THF (3 mL) was treated drop-wise with diethyl azodicarboxylate until a yellow color persisted. The resulting solution was stirred for 12 h at room temperature and then evaporated to afford a semisolid that was subjected to silica gel chromatography (hexane/acetone, 9:1) to afford 6 (463.0 mg, 68%) as a colorless oil. $^1$H NMR (300 MHz, CDCl$_3$) δ 7.73 (d, J=7.5 Hz, 2H), 7.59 (d, J=7.5 Hz, 2H), 7.42-7.25 (m, 4H), 6.25 (d, J=3.6 Hz, 1H), 5.67 (app. t, J=8.1 Hz, 1H), 5.53 (d, J=3.0 Hz, 1H), 4.78 (brd. s, 1H), 4.65 (d, J=12.3 Hz, 1H), 4.46-4.19 (m, 5H), 3.84 (t, J=9.3 Hz, 1H), 3.19 (m, 2H), 2.93-2.83 (m, 2H), 2.45-2.11 (m, 6H), 1.43-0.87 (m, 21H), 1.53 (s, 3H) ppm. $^{13}$C NMR (75 MHz, CDCl$_3$) 173.5, 169.4, 156.5, 144.1, 141.4, 138.8, 135.0, 130.7, 127.7, 127.1, 125.1, 120.4, 120.1, 81.2, 66.77, 66.71, 63.5, 60.21, 47.5, 42.9, 41.3, 36.9, 34.5, 30.2, 29.8, 29.7, 29.5, 29.4, 27.0, 26.0, 25.2, 24.8, 24.1, 18.3 ppm. ESI-MS m/z: 683 (M+H)$^+$.

14-[N-(Biotinyl)-12-aminododecanoxy]melampomagnolide B (4)

To a solution of 6 (150 mg, 0.30 mmol) in DMF (2 mL), was added TBAF (1M in THF, 0.30 mL), and the resulting solution stirred at ambient temperature for 30 min. In another flask, biotin-pentafluorphenol (0.435 mg, 0.22 mmol) was dissolved in DMF (2 mL) and this solution was added to the flask containing 6. The resulting solution was stirred for 12 h at room temperature and then evaporated to afford a sticky brown-colored gum. This residue was purified by silica gel column chromatography to afford 4 (silica neutralized with Et$_3$N), $CH_2Cl_2$/i-PrOH, (67.0 mg), 45% yield; white solid; 130-132° C.; $^1$H NMR (300 MHz, CDCl$_3$) δ 6.27 (d, J=3.3 Hz, 1H), 6.23 (s, 1H), 5.98 (t, J=5.5 Hz, 1H), 5.69 (t, J=8.4 Hz, 1H), 5.55 (d, J=3.3 Hz, 1H), 5.40 (s, 1H), 4.65 (d, J=12.6 Hz, 1H), 4.52 (m, 2H), 4.32 (m, 1H), 3.87 (t, J=9.3 Hz, 1H), 3.23 (m, 3H), 2.92 (m, 3H), 2.75 (d, J=15 Hz, 1H), 2.48-2.14 (m, 8H), 1.85-1.07 (m, 28H) 1.55 (s, 3H) ppm. $^{13}$C NMR (75 MHz, CDCl$_3$) δ 173.5, 172.8, 169.4, 138.8, 135.0, 130.6, 120.4, 81.2, 66.7, 63.5, 61.9, 60.34, 60.2, 59.1, 55.5, 42.9, 40.8, 39.8, 36.8, 36.3, 34.5, 34.2, 32.2, 29.99, 29.90, 29.7, 29.6, 29.5, 29.4, 28.3, 27.2, 26.0, 25.8, 25.2, 24.8, 24.1, 18.3 ppm; ESI-MS m/z: 688 (M+H)$^+$; Anal. Calcd. For $C_{37}H_{57}N_3O_7S$: C, 64.60; H, 8.35; N, 6.11. Found C, 64.63; H, 8.24; N, 6.15.

Example 2

Biological Assays

Streptavidin (SA) Beads Pull-Down Assay.

Treated cells were washed three times in cold PBS and lysed in Buffer F (10 mM Tris-HCl pH 7.5, 50 mM NaCl, 30 mM Sodium pyrophosphate, 50 mM NaF, 5 µM ZnCl2, 1% Triton X-100) with freshly added proteinase inhibitors (1 mM PMSF, 1×PIC, 0.1 mM Na$_3$OV$_4$). Lysates were cleared by 10 mins of 12,000 rpm spinning at 4° C. and the supernatant was incubated with SA beads for 2 hours on an end-to-end rotor at 4° C. Beads were then washed sequentially with 1×PBS, high salt wash buffer (500 mM NaCl in 0.1 M pH 5.0 NaOAc), low pH wash buffer (0.1 M pH 2.8 glycine-HCl), and one last time in 1×PBS. After the wash steps, the SA beads were boiled for 10 mins in 2×SDS-PAGE sample buffer to elute down all pull-down products.

Immunobloting.

Cell lysates or pull-down products were diluted in 5×SDS-PAGE sample buffer (10% w/v SDS, 10 mM DDT, 20% glycerol, 0.2M Tris-HCl, pH 6.8, 0.05% w/v bromophenol blue), and run on 8-10% SDSPAGE gels. Protein gels were then transferred to PVDF membrane and blocked with 5% milk in 0.1% TBST (20 mM Tris-HCl pH 7.5, 137 mM NaCl, 0.1% Tween 20), followed by incubation with antibodies against p-p65(ser 536) (Cell Signaling), IKK-β (Cell Signaling), p65 (Santa Cruz), β-actin (Sigma), or SA-HRP probe (Thermo).

Cell Viability Assays.

Cells treated with different concentrations of 1, 3 or 4 were washed with cold PBS and resuspended in 200 µL of Annexin binding buffer (10 mM HEPES/NaOH pH 7.4; 140 mM NaCl; 2.5 mM $CaCl_2$). Annexin-V and 7-amino-actinomycin (7-AAD) were added and the tubes were incubated at ambient temperature in the dark for 15 mins. Cells were then diluted with 200 μL of Annexin binding buffer and analyzed immediately by flow cytometry. Viable cells were scored as Annexin V negative/7-AAD negative. Percent viability data provided are normalized to untreated control specimens.

Example 3

MMB Derivative and Prodrug Stability Studies

Standard Curve and Quality Control Validation Solutions:
Stock solutions of prodrug and appropriate internal standard will be prepared in methanol. An HPLC standard curve with eight points will be prepared and utilized in the quantitative analysis of the unknown samples. Standard curve samples will be prepared by spiking buffers/SGF/SIF/blank plasma with prodrug, or parent drug working solutions. Calibration curves will be obtained using quadratic least-squares regression of area-under-the-curve (AUC) ratios (analyte peak AUC/internal standard peak AUC) versus prodrug and drug concentrations. The amount of prodrug, or parent drug in analytical samples can then be determined utilizing the standard curves.

Kinetics of Hydrolysis of the Prodrug in Aqueous Solutions (Non-Enzymatic):
A 0.02 M hydrochloric acid buffer, pH 1.3, as a non-enzymatic simulated gastric fluid; a 0.02 M sodium phthalate buffer, pH 5.2, a 0.02 M phosphate buffer, pH 7.4; and a 0.02 M boric acid and potassium chloride buffer, pH 9.7 will be used in this study. The pH 5.2 simulates intestinal fluid and the pH 7.4 simulates mouse plasma. pH 9.7 will be utillized to check the chemical stability of the linker moiety present in the prodrug. Reactions will be initiated by adding 5 mL of $1.0*10^{-3}$ M stock solution (in methanol) of the prodrug to 5 mL of appropriately thermostated (37±0.5° C.) aqueous solutions of the above buffer species. Aliquot-parts (300 μL) will be removed from the prodrug-buffer solutions at various time intervals, mixed with 50 μL of the 0.01M internal standard solution, and 20 μL of the resulting solution will be immediately injected onto an HPLC-DAD unit for quantitative analysis. Experiments will be run in triplicate.

Kinetics of Hydrolysis of the Prodrug in Simulated Gastric Fluid (SGF) and Simulated Intestinal Fluid (SIF) (Enzymatic Conditions):
Reactions will be initiated by adding 5 mL of $1.5*10^{-3}$ M stock solution (in methanol) of the prodrug to 5 mL of appropriately thermostated (37±0.5° C.) SGF and SIF solutions. Aliquot-parts (300 μL) of the resulting solutions will be removed at various time intervals, mixed with 50 μL of the 0.01M internal standard solution and immediately analyzed by HPLC-DAD. Experiments will be run in triplicate.

Kinetics of Hydrolysis of the Prodrug in Mouse Plasma (In Vitro):
For individual prodrugs, plasma from a single male BALB/C mouse will be obtained by centrifugation of blood obtained via cardiac puncture at 3000×g for 10-15 min. The supernatant plasma fraction (~0.8 mL) will be diluted with phosphate buffer (pH 7.4) to afford a total volume of 1 mL (80% mouse plasma). Incubations will be performed at 37±0.5° C. in a shaking water-bath. Reactions will be initiated by adding 50 μl, of stock solution of prodrug (1 mg/mL) to 1 mL of preheated (37° C.) 80% mouse plasma. Aliquot-parts (50 μL) will be taken at various times (6 time points, according to the observed stability data), mixed with 25 □L of a 0.01 M solution of an appropriate internal standard, and deproteinized by mixing with 300 μL of acetonitrile. After centrifugation for 5 min at 5000×g, the supernatant will be separated, dried under nitrogen gas, the residue reconstituted with 100 μL of methanol, and the resulting solution analyzed by HPLC-DAD. Analyses will be carried out in triplicate. HPLC analysis will utilize an Agilent 1100 series Quatpump equipped with a photodiode array detector and a computer integrating apparatus. A Waters Symmetry® C18 (5 μm, 3.9× 150 mm) column protected with a guard column (Nova-Pak® C18; 3.9×20 mm; 4μ) will be used as the stationary phase. Methanol/6 mM phosphate buffer containing 0.025% heptafluorobutyric acid (HFBA) with pH adjustment to 6.9 with triethylamine will be used as mobile phase. A 1.2 mL/min flow rate will be used; UV detection will be carried out at 220 nm.

Example 4

MMB Prodrug Pharmacokinetics and Bioavailability Studies

Assessment of plasma pharmacokinetics and bioavailability of the prodrug candidates is as follows. Mice will be treated with the appropriate prodrug candidate [5, 10 and 15 mg/kg po], and with 1 mg/kg iv of parent drug in a separate experiment (actual doses may vary, as determined from pilot experiments). Blood samples will be collected from jugular vein-catheterized mice at 0, 0.08, 0.25, 0.5, 1, 3, and 5 h, after oral prodrug administration; these timepoints may be adjusted if pilot results indicate that the proposed timepoints are inappropriate. All blood samples (150 μL) will be centrifuged at 4° C. for 5 min at 3000×g and the plasma fraction obtained will be stored at −20° C. until analyzed. The oral bioavailability of the prodrug (F) will be determined by comparing the plasma PK data obtained for the parent drug after oral dosing of the prodrug to that obtained after iv dosing of the parent drug, utilizing equation 1:

$$F=(AUC_{oral}/AUC_{iv})\times(Dose_{iv}/Dose_{oral})\times 100 \qquad \text{(Equation 1)}$$

where F is the percent absolute bioavailability, and $AUC_{oral}$, $AUC_{iv}$, $Dose_{oral}$, and $Dose_{iv}$ are the plasma area-under-the-curve and corresponding dose equivalent of the parent drug after oral administration of the prodrug, and the plasma area-under-the-curve and dose of the parent drug after iv administration, respectively.

The F value for the most desirable prodrugs will be ideally≥60-80%, but values in the range 30-60% may also be acceptable.

For plasma analysis, acetonitrile (300 μL) will be added to 50 μL of mouse plasma, the sample vortexed for 2 min, and centrifuged (5000×g, 5 min, 4° C.). Supernatant will be evaporated to dryness under nitrogen. Residues will be reconstituted with 0.2 mL of HPLC mobile phase. Reconstituted samples (20 μL) will be analyzed on a 1200L Quadrupole LC/MS/MS unit (Varian Analytical Inst) for the presence of parent drug and prodrug. Detection will be by positive electrospray ionization (ESI) MS, and MMB and prodrug plasma concentrations will be determined utilizing deuterated internal drug standards (from in-house synthesis). We have found that HPLC/MS/MS can provide sensitivity that is comparable to the use of [$^{14}$C]-labeled analytes.

Example 5

Assay for Antileukemic Activity

For apoptosis analysis, one million primary acute myelogenous leukemia (AML) cells are washed with cold PBS and resuspended in 200 microliters of Annexin binding buffer (10 mM HEPES/NaOH pH 7.4; 140 mM NaCl; 2.5 mM $CaCl_2$). Annexin V-FITC (Pharmingen) and 0.25 mg/mL 7-AAD (7-aminoactinomycin D, Molecular Probes, CA) were added and the tubes are incubated at room temperature in the dark for 15 minutes. Cells are then diluted with 200 microliters of Annexin binding buffer and analyzed immediately by flow cytometry. Viable cells are identified as failing to label with Annexin V or 7-AAD. Cells beginning to die label with Annexin V, and as membrane integrity is lost, will also label with 7-AAD. For each MMB derivative, the percentage of viable cells is determined after 24 hours of culture at a 10 micromolar concentration. Data are normalized to untreated control specimens. Healthy human bone marrow cells are also used in the above assay to test the cytotoxicity of MMB and derivatives.

Example 6

Analysis of MMB and Derivatives Using Human-Mouse Xenografts

To assess the effect of MMB derivatives on primary human stem cell populations, experiments are conducted using transplantation into immune deficient NOD/SCID mice. Successful engraftment of NOD/SCID bone marrow at 6-8 weeks post-transplant has been shown to be a measure of stem cell content for human hematopoietic cell populations (Lapidot et al., *J Mol Med.* 1997; 75: 664-673; Dick, *Curr Opin Hematol.* 1996; 3:405-409). For each experiment, cryopreserved mononuclear cell specimens from normal or AML donors are thawed, and treated in vitro with 7.5 micromolar MMB derivative for 12-18 hours. Following culture, 5-10 million cells/animal are injected intravenously into sublethally irradiated (300 Rad) NOD/SCID mice. After 6-8 weeks, animals are sacrificed and bone marrow is analyzed for the presence of human cells using flow cytometry as previously described (Guzman et al., *Proc Natl Acad Sci USA* 2002; 99: 16220-162253). Human specific antibodies for CD45 are used to assess the level of total engraftment.

Example 7

MTS-PMS Assay

A 96-well U-bottomed plate (Becton Dickinson Labware, Franklin Lakes, N.J.) at a concentration of 5,000 cells per 50 microliters (mL) of media is incubated in 5% $CO_2$ at 37° C. for 24 hours. Varying compound concentrations in 50 mL of media are added to the media 24 hours later, for example, the cancer cell line is treated with increasing concentrations of MMB and MMB-derivative. Colorimetric readings are obtained using the MTS/PMS system and an ELISA plate reader, after 48 hours of exposure to test compounds. The readings obtained for each concentration tested are from an average of eight wells. Each experiment is expressed as a percentage of the solvent control and completed at least three times. Various cancer cell lines are employed. The hormone refractory prostate cancer cell line CWR22Rv1; lung cancer cell lines A549, H460, H-23 and H522 can be employed in this assay.

Example 8

Clonogenic Assay

Initially, 100 cells growing in log phase are plated per 3 ml of media in each well of a six well plate. After 24 hrs of plating of the cells the test compound is added at varying concentrations. At 24 and 96 hours after addition of drug, the media is changed. Hence, the cells were are exposed to the drug for 24 hrs. When cell colonies appear at Day 15 they are stained by Sure Stain Dye and counted. For example, the hormone refractory prostate cancer cell line CWR22Rv1 is treated with increasing concentrations of MMB derivatives for three hours. Cellular proliferation is evaluated in the clonogenic assay. Alternatively, another cancer cell line can be employed, such as, for example, hbl-100, mdl-231 and 436 cells Example 9 cDNA Array Analysis

Total cellular RNA is extracted from the human monocyte cell line THP-1 under three conditions 2 hours after Time 0:
1) Control is added at Time 0
2) Lipopolysacchride (10 nM) is added at Time plus one (1) hour
3) At Time 0, 10 micromoles of test compound is added and then at Time+1 LPS (10 nM) is added.

RNA is extracted using RNeasy Min Kit (Qiagen, USA) according to the manufacturer's instructions. The Human Drug Targets for Inflammation and Immunomodulation Q series GE array kit (HS-048-12) is obtained from SuperArray Bioscience Corporation (Frederick, Md.). The kit determines expression of 96 genes that are associated with inflammation. RNA from respective samples was used as a template to generate biotin labeled cDNA probes using GEArray Ampo-labelling RT kit (SuperArray, Bioscience Corp., USA). The cDNA probes corresponding to the mRNA population are then denatured and hybridization is carried out in GEHyb solution to nylon membranes spotted with gene specific fragments. Membranes are then washed in 2×SSC, 1% SDS twice for 15 minutes each, followed by 0.1 SSC, 0.5% SDS twice for 15 minutes each. Chemiluminescence is used to visualize the expression levels of each transcript and the results were quantified with the GEArray Analyzer. The change in a given gene transcript is estimated by normalizing the signal intensities with the signal derived from PPIA and with minimum background subtraction. Transcription of certain genes is increased after pre-treatment with LPS. Pretreatment with test compound is evaluated in a comparative fashion to detect any change in gene transcription induced by LPS.

Example 10

Electrophoretic Mobility Gel Shift Assay

Each cancer cell line in exponential growth phase is treated with solvent control or various concentrations of MMB derivatives dissolved in 100% ethanol for 3 hours prior to harvesting. Cells are harvested and whole cell extracts are prepared as described previously (Nakshatri et al., *Mol Cell Biol*, 17: 3629-3639, 1997; Sweeney et al., Clin Cancer Res, 10: 5501-5507, 2004). Extracts are incubated with a radiolabelled NFκB probe for 30 minutes at room temperature. The oligonucleotide probe binds to the NFκB DNA binding site in the promoter region of the immunoglobulin gene. Electrophoresis and autodioragraphy are performed as described previously (Nakshatri et al., 1997) using NFκB and SP-1 probes (Promega, Madison, Wis.). The specificity of MMB and derivative inhibition of NFκB DNA binding is verified by the use of the SP-1 probe as a control. Identification of the NFκB subunits binding to DNA and inhibited by test compounds is identified by gel supershift. For example, lung cancer cell lines A-549, H-23, H-522, and H-460 can be employed. All four non-small lung cancer cells were treated with increasing concentrations of test compound for three hours, and NF-κB DNA binding is measured by electrophoretic mobility shift assay (EMSA) as described. Cancer cell lines HT-1376, UMUC-3, CWR22Rv1 can also be employed.

Example 11

Pretreatment of Radiation Sensitive Cell Line A549

The radiation sensitive cell line A549 is pretreated with MMB concentrations ranging from, e.g., 0 to 2.5 micromolar. The cells are then subjected to ionizing radiation doses ranging from 0-6Gy and survival fraction of the cells determined. Results are evaluated for MMB induced radiation sensitivity to the cells compared to cells not receiving pre-treatment with MMB.

Example 12

TRAIL Induced Apoptosis Assay

MDA-MB-231 breast cancer cells ($2 \times 10^5$ cells in 60 mm plates) are treated first with 2 or 5 μM of MMB or test compound. After two hours, TRAIL (TNF related-apoptosis-inducing-ligand, 5 ng/ml) or TRAIL-R11-activating antibodies (10 ng/ml) are added. After 48 hours of TRAIL or TRAIL-RII antibody treatment, cells are harvested and apoptosis is measured using carboxyfluorescein-FLICA assay. Briefly, both attached and floating cells are collected by trypsinization, incubated with carboxyfluorescein-labeled pan-caspase inhibitor FAM-VAD-FMK for 2 h at 37° C. Labeled cells are rinsed twice in PBS and re-suspended in 300 μl of PBS containing 0.3 μg of propidium iodide. Apoptotic cells are identified by FACScan analysis. Live cells do not stain; FAM-VAD-FMK stains apoptotic cells. Apoptotic cells that have lost plasma membrane integrity are stained by both FAM-VAD-FMK and propidium iodide. Necrotic cells are stained only by propidium iodide. MDA-MB-231 cells are relatively resistant to TRAIL. However, they are evaluated for change in sensitivity to TRAIL or TRAIL-RII activating antibody-induced apoptosis and atypical apoptosis upon pre-treatment with test compound.

We claim:

1. A melampomagnolide B derivative compound of the formula (I):

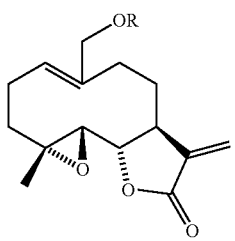

(I)

wherein:
R is selected from —P(O)(OR$^1$)(OR$^2$); —CH$_2$OP(O)(OR$^1$)(OR$^2$); —C(O)(CR$^3$R$^4$)$_n$X; —CH$_2$OC(O)(CR$^3$R$^4$)$_n$X; —C(O)O(CR$^3$R$^4$)$_n$X; —C(O)NHCH$_2$CH$_2$NH$_2$; —C(O)NHCH$_2$(CH$_2$)$_2$NH$_2$; —C(O)NHCH$_2$(CH$_2$)$_3$NH$_2$; —C(O)NHCH$_2$(CH$_2$)$_4$NH$_2$ and —C(O)(CH$_2$)$_m$C(O)NH(CR$^3$R$^4$)$_n$X;

R$^1$, R$^2$ are independently selected from H; Na; K; NH$_3$; unsubstituted C$_1$-C$_{12}$alkyl, optionally substituted alkenyl, alkynyl, heterocycloalkyl, heteroaryl, cycloalkyl, and aryl;

R$^3$, R$^4$ are independently selected from H, NR$^5$R$^6$, OR$^1$, SR$^1$, S(O)R$^1$, SO$_2$R$^1$, optionally substituted C$_1$-C$_{12}$alkyl, alkenyl, alkynyl, heterocycloalkyl, heteroaryl, cycloalkyl, and aryl;

R$^5$, R$^6$ are independently selected from H; optionally substituted C$_1$-C$_{12}$alkyl, alkenyl, alkynyl, heterocycloalkyl, heteroaryl, cycloalkyl, aryl; —CO$_2$C$_1$-C$_{12}$alkyl, CO$_2$alkenyl, CO$_2$alkynyl, CO$_2$heterocycloalkyl, CO$_2$heteroaryl, CO$_2$cycloalkyl, CO$_2$aryl; and C$_1$-C$_{12}$alkylamino; or R$^5$ and R$^6$ optionally together with the nitrogen atom form an optionally substituted 5-12 membered ring, said ring optionally comprising 1 or more heteroatoms;

X is selected from NR$^5$R$^6$, NHC(O)R$^2$; NHC(O)OR$^2$; OR$^1$, SR$^1$, halo, trifluoromethyl, optionally substituted C$_1$-C$_{12}$alkyl, alkenyl, alkynyl, heterocycloalkyl, heteroaryl, cycloalkyl, and aryl;

n is 1-6, m is 1-2; or a pharmaceutically acceptable salt or ester thereof.

2. The compound of claim 1 wherein R is selected from —P(O)(OR$^1$)(OR$^2$) and —CH$_2$OP(O)(OR$^1$)(OR$^2$).

3. The compound of claim 2 wherein R$^1$, R$^2$ are independently selected from H, Na, and optionally substituted C$_1$-C$_6$ alkyl.

4. The compound of claim 3 wherein R is selected from

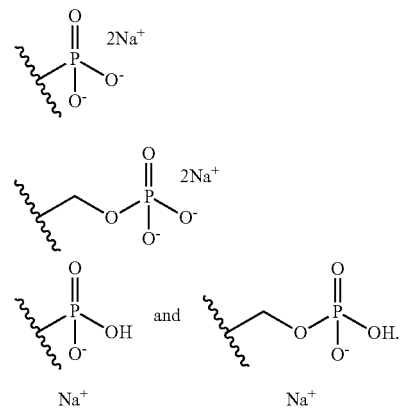

5. The compound of claim 1 wherein R is selected from —C(O)(CR$^3$R$^4$)$_n$X; C(O)NHCH$_2$CH$_2$NH$_2$; —C(O)NHCH$_2$(CH$_2$)$_2$NH$_2$; —C(O)NHCH$_2$(CH$_2$)$_3$NH$_2$; and —C(O)NHCH$_2$(CH$_2$)$_4$NH$_2$.

6. The compound of claim 5 wherein X is selected from NR$^5$R$^6$, OR$^1$, and SR$^1$.

7. The compound of claim 6 wherein R is selected from

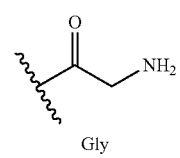

Gly

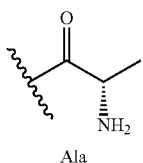
Ala

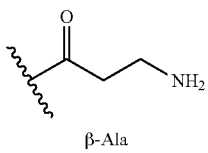
β-Ala

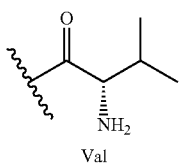
Val

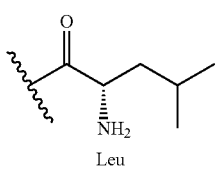
Leu

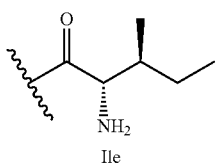
Ile

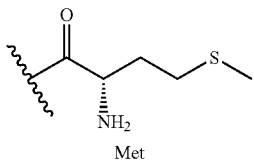
Met

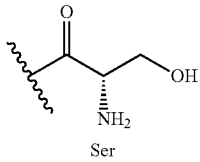
Ser

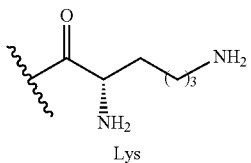
Lys

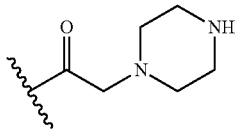
and

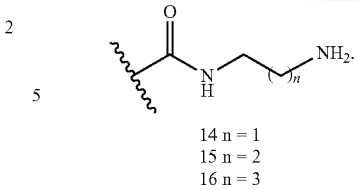

14 n = 1
15 n = 2
16 n = 3
17 n = 4

8. The compound of claim 1 wherein R is —CH$_2$OC(O)(CR$^3$R$^4$)$_n$X.

9. The compound of claim 8 wherein X is NR$^5$R$^6$.

10. The compound of claim 9 wherein R is selected from

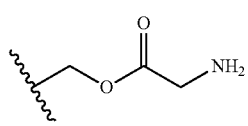

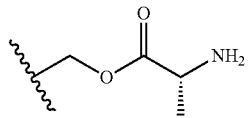
and

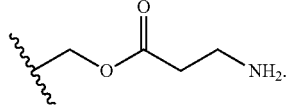

11. The compound of claim 1 wherein R is —C(O)O(CR$^3$R$^4$)$_n$X.

12. The compound of claim 11 wherein X is NR$^5$R$^6$.

13. The compound of claim 12 wherein R is selected from

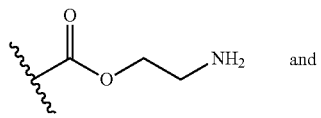
and

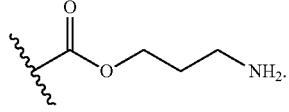

14. The compound of claim 1 wherein R is —C(O)(CH$_2$)$_m$C(O)NH(CR$^3$R$^4$)$_n$X.

15. The compound of claim 14 wherein X is NR$^5$R$^6$.

16. The compound of claim 15 wherein R is selected from

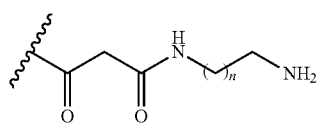

22 n = 1
23 n = 2

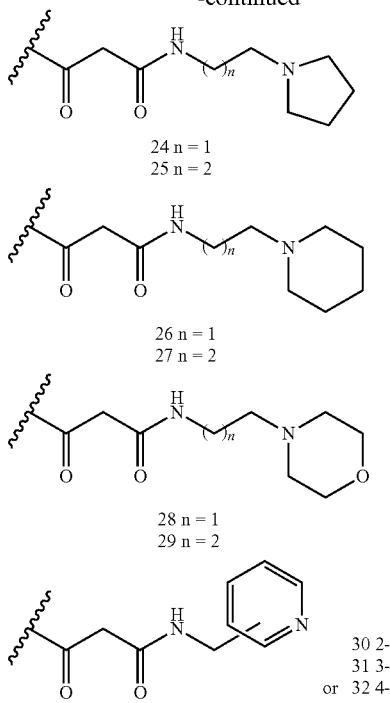

24 n = 1
25 n = 2

26 n = 1
27 n = 2

28 n = 1
29 n = 2

30 2-pyr
31 3-pyr
or 32 4-pyr.

17. The compound of claim 1 wherein $R^5$ and $R^6$ together with N form an optionally substituted 5-12 membered ring.

18. The compound of claim 17 wherein said ring is a monocyclic, bicyclic or tricyclic alkyl or aryl ring system, said ring system optionally substituted and optionally comprising one or more heteroatoms or a group selected from —CO, —SO—, —SO$_2$—, and —PO—.

19. The compound of claim 18 wherein $R_1$ and $R_2$ are $(CH_2)_a$-Y-$(CH_2)_b$—; where Y is a heteroatom or a group selected from —CO—, —SO—, —SO$_2$—, and —PO—; a is an integer 0 to 5; b is an integer 0 to 5; the sum of a and b being 0 to 5.

20. The compound of claim 1 wherein X is $NR^5R^6$, and the compound is a pharmaceutically acceptable salt selected from hydrochloride, maleate, fumarate, or mesylate.

21. A pharmaceutical composition comprising a compound of claim 1 or a pharmaceutically acceptable salt thereof; in combination with a pharmaceutically effective diluent or carrier.

22. A melampomagnolide B derivative compound of formula (I):

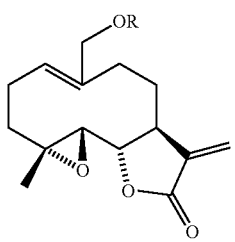

(I)

wherein R is a group that is cleaved to a hydroxyl group under physiological conditions during or after administration to a mammalian patient, thereby yielding Melampomagnolide B; wherein R is selected from —P(O)(OR$^1$)(OR$^2$); —CH$_2$OP(O)(OR$^1$)(OR$^2$); —C(O)(CR$^3$R$^4$)$_n$X; —CH$_2$OC(O)(CR$^3$R$^4$)$_n$X; —C(O)O(CR$^3$R$^4$)$_n$X; —C(O)NHCH$_2$CH$_2$NH$_2$; —C(O)NHCH$_2$(CH$_2$)$_2$NH$_2$; —C(O)NHCH$_2$(CH$_2$)$_3$NH$_2$; C(O)NHCH$_2$(CH$_2$)$_4$NH$_2$ and —C(O)(CH$_2$)$_m$C(O)NH(CR$^3$R$^4$)$_n$X;

$R^1$, $R^2$ are independently selected from H; Na; K; NH$_3$; optionally substituted C$_1$-C$_{12}$alkyl, alkenyl, alkynyl, heterocycloalkyl, heteroaryl, cycloalkyl, and aryl;

$R^3$, $R^4$ are independently selected from H, NR$^5$R$^6$, OR$^1$, SR$^1$, S(O)R$^1$, SO$_2$R$^1$, optionally substituted C$_1$-C$_{12}$alkyl, alkenyl, alkynyl, heterocycloalkyl, heteroaryl, cycloalkyl, and aryl;

$R^5$, $R^6$ are independently selected from H; optionally substituted C$_1$-C$_{12}$alkyl, alkenyl, alkynyl, heterocycloalkyl, heteroaryl, cycloalkyl, aryl; —CO$_2$C$_1$-C$_{12}$alkyl, CO$_2$alkenyl, CO$_2$alkynyl, CO$_2$heterocycloalkyl, CO$_2$heteroaryl, CO$_2$cycloalkyl, CO$_2$aryl; and C$_1$-C$_{12}$alkylamino; or $R^5$ and $R^6$ optionally together with the nitrogen atom form an optionally substituted 5-12 membered ring, said ring optionally comprising 1 or more heteroatoms;

X is selected from NR$^5$R$^6$, OR$^1$, SR$^1$, halo, trifluoromethyl, unsubstituted C$_1$-C$_{12}$alkyl, optionally substituted alkenyl, alkynyl, heterocycloalkyl, heteroaryl, cycloalkyl, and aryl;

n is 1-6, m is 1-2; or a pharmaceutically acceptable salt or ester thereof.

23. The compound of claim 1 wherein $R^1$ is selected from H; Na; K; NH$_3$; optionally substituted C$_1$-C$_{12}$alkyl, alkenyl, alkynyl, heterocycloalkyl, heteroaryl, cycloalkyl, and aryl;

$R^2$ is selected from H; Na; K; NH$_3$; unsubstituted C$_1$-C$_{12}$alkyl, alkenyl, alkynyl, heterocycloalkyl, heteroaryl, cycloalkyl, and aryl;

$R^5$, $R^6$ are independently selected from H; unsubstituted C$_1$-C$_{12}$alkyl, or unsubstituted heterocycloalkyl; optionally substituted alkenyl, alkynyl, heterocycloalkyl, heteroaryl, cycloalkyl, aryl; —CO$_2$C$_1$-C$_{12}$alkyl, CO$_2$alkenyl, CO$_2$alkynyl, CO$_2$heterocycloalkyl, CO$_2$heteroaryl, CO$_2$cycloalkyl, CO$_2$aryl; and C$_1$-C$_{12}$alkylamino; or $R^5$ and $R^6$ optionally together with the nitrogen atom form an optionally substituted 5-12 membered ring, said ring optionally comprising 1 or more heteroatoms;

X is selected from NR$^5$R$^6$, NHC(O)R$^2$; NHC(O)OR$^2$; OR$^1$, SR$^1$, halo, trifluoromethyl, unsubstituted C$_1$-C$_{12}$alkyl, optionally substituted alkenyl, alkynyl, heterocycloalkyl, heteroaryl, cycloalkyl, and aryl.

* * * * *